US009085805B2

(12) United States Patent
von Bubnoff et al.

(10) Patent No.: US 9,085,805 B2
(45) Date of Patent: Jul. 21, 2015

(54) METHODS AND COMPOSITIONS FOR DIAGNOSING GASTROINTESTINAL STROMAL TUMORS

(75) Inventors: Nikolas von Bubnoff, Freiburg (DE); Thoralf Lange, Leipzig (DE); Jacqueline Maier, Leipzig (DE)

(73) Assignee: Albert-Ludwigs-Universität Freiburg, Freiburg im Breisgau (DE)

( * ) Notice: Subject to any disclaimer, the term of this patent is extended or adjusted under 35 U.S.C. 154(b) by 0 days.

(21) Appl. No.: 13/994,010

(22) PCT Filed: Jun. 28, 2011

(86) PCT No.: PCT/EP2011/060846
§ 371 (c)(1),
(2), (4) Date: Nov. 13, 2013

(87) PCT Pub. No.: WO2012/001007
PCT Pub. Date: Jan. 5, 2012

(65) Prior Publication Data
US 2014/0065630 A1 Mar. 6, 2014

(30) Foreign Application Priority Data
Jun. 28, 2010 (EP) .................................. 10167588

(51) Int. Cl.
*C12Q 1/68* (2006.01)
(52) U.S. Cl.
CPC ............... *C12Q 1/6886* (2013.01); *C12Q 1/68* (2013.01); *C12Q 2600/156* (2013.01); *C12Q 2600/16* (2013.01)
(58) Field of Classification Search
CPC ...................................................... C12Q 1/68
See application file for complete search history.

(56) References Cited

U.S. PATENT DOCUMENTS

| 2007/0254295 | A1 | 11/2007 | Harvey et al. | |
|---|---|---|---|---|
| 2012/0082659 | A1* | 4/2012 | Land et al. | 424/130.1 |
| 2013/0045191 | A1* | 2/2013 | Weinschenk et al. | 424/93.71 |

FOREIGN PATENT DOCUMENTS

| WO | WO 01/42504 | 6/2001 |
|---|---|---|
| WO | WO 2012/001007 | 1/2012 |

OTHER PUBLICATIONS

Lasota J, Miettinen M. Clinical significance of oncogenic KIT and PDGFRA mutations in gastrointestinal stromal tumours. Histopathology. Sep. 2008;53(3):245-66. Epub Feb. 28, 2008.*
Martin J et al.; Spanish Group for Sarcoma Research. Deletions affecting codons 557-558 of the c-KIT gene indicate a poor prognosis in patients with completely resected gastrointestinal stromal tumors: a study by the Spanish Group for Sarcoma Research (GEIS). J Clin Oncol. Sep. 1, 2005;23(25):6190-8.*
Pelz-Ackermann O, Cross M, Pfeifer H, Deininger M, Wang SY, Al-Ali HK, Niederwieser D, Lange T. Highly sensitive and quantitative detection of BCR-ABL kinase domain mutations by ligation PCR. Leukemia. Dec. 2008;22(12):2288-91. Epub Jul. 10, 2008.*
Gasparotto D, Rossi S, Bearzi I, Doglioni C, Marzotto A, Hornick JL, Grizzo A, Sartor C, Mandolesi A, Sciot R, Debiec-Rychter M, Dei Tos AP, Maestro R. Multiple primary sporadic gastrointestinal stromal tumors in the adult: an underestimated entity. Clin Cancer Res. Sep. 15, 2008;14(18):5715-21. Epub Sep. 8, 2008.*
Heinrich et al., Journal of Clinical Oncology, vol. 21, No. 23, (2003) pp. 4342-4349.*
Office Action corresponding to European Patent Application No. 11 727 706.1 dated Apr. 7, 2014.
Corless et al., "Molecular pathobiology of gastrointestinal stromal sarcomas," Annual Review of Pathology—Mech Dis, vol. 3, pp. 557-586 (2008).
Maier et al., Detection of Mutant Free Circulating Tumor DNA in the Plasma of Patients with Gastrointestinal Stromal Tumor Harboring Activating Mutations of CKIT or PDGFRA, Clinical Cancer Research, pp. OF1-OF14 (2013).
Antoch, G. et al. (2004) J. Nucl. Med. 45, 357-365.
Bauer, S. et al. (2005) Int. J. Cancer, 117, 316-325.
Benson, D.A., et al. (2008) Nucl. Acids Res., 36, D25-D30.
Blanke, C.D., et al. (2008) J. Clin. Oncol., 26, 626-632.
Corless et al., "PDGFRA mutations in gastrointestinal stromal tumors: frequency, spectrum and in vitro sensitivity to imatinib," Journal of Clinical Oncology : Official Journal of the American Society of Clinical Oncology, vol. 23, No. 23, pp. 5357-5364 (Aug. 10, 2005).
Demetri, G.D., (2006) Lancet 368, 7329-1338.
Gambhir, S.S., et al. (2001.) J. Nucl. Med. 42, 1S-93S.
GenBank Accession No. NM_000222.2.
GenBank Accession No. NM_006206.4.
Gormally et al., "Circulating free DNA in plasma or serum as biomarker of carcinogenesis: Practical aspects and biological significance", Mutation Research, vol. 635, No. 2-3, pp. 105-117 (May 2007).
Hirota, S., et al. (1998) Science, 279, 577-580.

(Continued)

*Primary Examiner* — Ardin Marschel
(74) *Attorney, Agent, or Firm* — Jenkins, Wilson, Taylor & Hunt, P.A.

(57) ABSTRACT

The present invention relates to an in vitro method for diagnosing and/or monitoring in a subject a gastrointestinal stromal tumor or a predisposition to develop a gastrointestinal stromal tumor, comprising detecting and/or analyzing in a test sample derived from the subject one or more mutations at the DNA level in any one or both of the marker genes cKIT (GenBank acc. no. NM_000222.2) and PDGFRA (GenBank acc. no. NM_006206.4), wherein the DNA is circulating DNA, and wherein the presence of any one of the mutations detected in the test sample is indicative of a gastrointestinal stromal tumor or a predisposition to develop a gastrointestinal stromal tumor in the subject. The present invention is also directed to a corresponding kit-of-parts for diagnosing and/or monitoring a gastrointestinal stromal tumor or a predisposition to develop a gastrointestinal stromal tumor, comprising means for detecting and/or analyzing one or more mutations as defined herein, as well as to the use of one or more mutations as defined herein as a panel of molecular markers for diagnosing and/or monitoring a gastrointestinal stromal tumor or a predisposition to develop a gastrointestinal stromal tumor.

13 Claims, 8 Drawing Sheets

(56) References Cited

OTHER PUBLICATIONS

Hirota, S., et al. (2003) Gastroenterology, 125, 660-667.
International Search Report corresponding to International Applicatin No. PCT/EP2011/060846 dtaed Oct. 24, 2011.
Lux Marcia et al., "KIT extracellular and kinase domain mutations in gastrointestinal stromal tumors," American Journal of Pathology, vol. 156, No. 3, pp. 791-795, (Mar. 2000).
Rubin et al., "KIT activation is a ubiquitous feature of gastrointestinal stromal tumors," Cancer Research, vol. 61, No. 22, pp. 8118-8121 (Nov. 15, 2001).
Shapiro et al., "Determination of Circulating DNA Levels in Patients With Benign or Malignant Gastrointestinal Disease," Cancer, American Cancer Society, vol. 51, No. 11, pp. 2116-2120 (Jan. 1, 1983).
Verweij, J. et al. (2004) Lancet, 364, 1127-1134.
Diehl et al., "Circulating mutant DNA to Assess tumor dynamics," Nat. Med., vol. 14, No. 9, pp. 985-990 (Sep. 2008).
Hanash et al., "Emerging molecular biomarkers—blood-based strategies to detect and monitor cancer," Nat. Rev. Clin. Oncol., vol. 8, pp. 142-150 (2011).
Kimura et al., "Detection of Epidermal Growth Factor Receptor Mutations in Serum as a Predictor of the Response to Gefitinib in Patients with Non-Small-Cell Lung Cancer," Clin. Cancer Res., vol. 12, No. 13, (Jul. 1, 2006).
Sidransky, "Emerging Molecular Markers of Cancer", Nature Reviews, vol. 2, pp. 210-219 (2002).
Sozzi et al., "Quantification of Free Circulating DNA as a Diagnostic Marker in Lung Cancer," Journal of Clinical Oncology, vol. 21, No. 21, pp. 3902-3908 (Nov. 1, 2003).

\* cited by examiner

A

B

A

B

Imatinib start

A

B

METHODS AND COMPOSITIONS FOR DIAGNOSING GASTROINTESTINAL STROMAL TUMORS

FIELD OF THE INVENTION

The present invention relates to methods and compositions for diagnosing and/or monitoring gastrointestinal stromal tumors or a predisposition to develop such condition. The methodological approach is based on the detection and/or (quantitative) analysis of one or more of tumor-specific mutations in the marker genes cKIT and PDGFRA, in particular in circulating DNA samples.

BACKGROUND

Gastrointestinal stromal tumors (GISTs) are one of the most common mesenchymal tumors of the gastrointestinal tract (about 1-3% of all gastrointestinal malignancies). Approximately 85% of the GISTs harbor activating (i.e. gain-of-function) mutations in cKIT gene encoding a stem cell factor receptor having tyrosine kinase activity. Furthermore, about 35% of the GISTs with a wild-type cKIT gene instead have mutations in another gene, PDGFRA (platelet derived growth factor receptor-alpha), which is a related tyrosine kinase (reviewed, e.g., in. Corless, C. L. and Heinrich, M. C. (2008) *Annu. Rev. Pathol.* 3, 557-586). These mutations are an early event in GIST progression.

The onco-proteins cKIT and PDGFRA serve as targets for the small molecule tyrosine kinase inhibitors such as imatinib and sunitinib. Notably, treatment with imatinib is not curative unless complete resection of the tumor is possible. In advanced, metastasized or irresectable GISTs, a partial remission can be attained in about 50% of the patients treated with imatinib. However, most patients still experience disease progression while receiving imatinib (see, e.g., Verweij, J. et al. (2004) *Lancet* 364, 1127-34; Blanke, C. D. et al. (2008) *J. Clin. Oncol.* 26, 626-632). In addition, such patients were also found to only transiently respond to sunitinib (Demetri, G. D. et al. (2006) *Lancet* 368, 1329-1338).

Even though imatinib and sunitinib exhibited remarkable clinical effects, their efficacies greatly depend on the genotype of the GIST. The drugs met intrinsic or acquired resistance during the treatment, of which the molecular mechanisms were mostly dependent on the genotype of GIST as well, including primary mutations or secondary mutations in the kinase domains of the corresponding target genes, respectively. Thus, advanced GISTs may require multidisciplinary treatment.

From the above it is immediately evident that a necessary prerequisite for a successful therapy of GISTs is the provision of accurate methods for diagnosing, staging and/or monitoring progression of such tumors, which, in turn, enable a reliable prognosis and risk assessment, and thus the selection of an appropriate therapy.

One diagnostic approach relies on immunohistochemistry, in particular on the staining of cKIT by means of specific antibodies. However, about 5-10% of the GISTs are cKIT negative. Hence, cKIT staining does not result in the reliable detection of all GISTS; additional and/or alternative methods are required Various imaging methods are used for staging or monitoring GIST progression including positron emission-tomography (PET), computed tomography (CT), magnetic resonance tomography, and combinations thereof such as PET-CT. The most sensitive imaging technique currently available is 2-deoxy-2-($^{18}$F)fluoro-D-glucose positron emission-tomography (FDG-PET). However, the specificity and sensitivity of this method is limited so that, for example, small tumors or residual tumor activity after onset of therapy may be missed (Gambhir, S. S. et al. (2001) *J. Nucl. Med.* 42, 1S-93S; Antoch, G. et al. (2004) *J. Nucl. Med.* 45, 357-365). Furthermore, even in cases with complete response to a given therapy, lesions in most cases still contain viable tumor (Bauer, S. et al. (2005) *Int. J. Cancer* 117, 316-25). Thus, it is currently not possible to measure residual disease in PET-CT responders, and the trigger to change treatment is clinical or PET/CT-morphologic progression. In addition, FDG-PET (as well as other imaging methods) requires sophisticated analytical instrumentation, which is expensive both in terms of initial cost and maintenance, as well as trained personnel. This makes such systems unsuitable for routine medical practices, "bedside" testing, or in remote locations.

Accordingly, there still remains a need for improved methods and compositions that enable the rapid, reliable and cost-saving diagnosis, staging, and monitoring of gastrointestinal stromal tumors or a predisposition to develop such condition.

Thus, it is an object of the present invention to provide such methods and compositions for the diagnosis and monitoring of GISTs.

SUMMARY OF THE INVENTION

In one aspect, the present invention relates to an in vitro method for diagnosing and/or monitoring in a subject a gastrointestinal stromal tumor or a predisposition to develop a gastrointestinal stromal tumor, comprising detecting and/or analyzing in a test sample derived from the subject one or more mutations at the DNA level in any one or both of the marker genes cKIT (GenBank acc. no. NM_000222.2) and PDGFRA (GenBank acc. no. NM_006206.4), wherein the DNA is circulating DNA, and wherein the presence of any one of the mutations detected in the test sample is indicative of a gastrointestinal stromal tumor or a predisposition to develop a gastrointestinal stromal tumor in the subject.

In some embodiments, the test sample used is a blood sample, preferably a plasma sample.

In specific embodiments, the method further comprises comparing the results obtained in the test sample with those obtained in a control sample.

In preferred embodiments, the DNA is circulating plasma DNA.

In further preferred embodiments, the method further comprises quantifying the amount of mutated DNA present in the test sample, wherein optionally an elevated amount of mutated DNA in the test sample is indicative of gastrointestinal stromal tumor progression.

Preferably, the one or more mutations are located in any one or more of the regions corresponding to the codons 456-508, 549-599, 642-654, 670-709, 786-823, and 829 of the cKIT marker gene (GenBank acc. no. NM_000222.2) and/or in any one or more of the regions corresponding to the codons 478, 561-571, 687, and 824-846 in the PDGFRA marker gene (GenBank acc. no. NM_006206.4).

In other preferred embodiments, the one or more mutations in the cKIT marker gene (GenBank acc. no. NM_000222.2) are selected from the group consisting of: a deletion of any one or more of the nucleotide sequences corresponding to codons 550-558, 551-554, 553-558, 554-571, 557-558, 558-559, 559-560, 560-578, 574-580, and 578; a deletion of the nucleotide sequence corresponding to codons 554-561 combined with the nucleotide insertion CTT; a deletion of the nucleotide sequence corresponding to codons 555-572 combined with the nucleotide insertion G; a deletion of the nucleotide sequence corresponding to codons 559-560 combined with the nucleotide substitution AAG→AGG at codon 558; a duplication of any one or more of the nucleotide sequences corresponding to codons 502-503 and 573-591; an insertion of the nucleotide sequence ACCAACACAACT TCCTTAT-GATCACAAATGGGAGTTTCCCAGAAA-CAGGCTGAGTTTTGG (SEQ ID NO: 10) at codons 573-592; an insertion of the nucleotide sequence GCAAACAACACAACTTCCTTATGATCAC AAATGG-GAGTTTCC (SEQ ID NO: 11) at codon 585; an insertion of the nucleotide sequence TCCCAACA CAACTTCCTTAT-GATCACAAATGGGAGTTTCCCA (SEQ ID NO: 12) at codon 586; an insertion of the nucleotide sequence ACAACT-TCCTTATGATCACAAATGGGAGTTTC-CCAGAAACAGGCT (SEQ ID NO: 13) at codon 589; and any one or more of the nucleotide substitutions TGG→CGG and TGG→GGG at codon 557; AAG→CCG, AAG→AAC/T, AAG→ACG, and AAG→AGG at codon 558; GTT→GAT, GTT→GCT, GTT→GGT, and GTT→GANG at codon 559; GTT→GAT, GTT→GANG, and GTT→GGT at codon 560; AAA→GAA at codon 642; GTG→GCG at codon 654; and GAC→GTC and GAC→TTC at codon 816.

In further preferred embodiments, the one or more mutations in the PDGFRA marker gene (GenBank acc. no. NM_006206.4) comprise the nucleotide substitution GAC→GTC at codon 842; and a deletion of the nucleotide sequence corresponding to codons 542-546.

In some embodiments, the detection and/or analysis of the one or more mutations is performed by an allele-specific method, preferably by ligation-PCR.

In some other embodiments, the method is performed in a multiplex format.

In another aspect, the present invention relates to a kit-of-parts for diagnosing and/or monitoring a gastrointestinal stromal tumor or a predisposition to develop a gastrointestinal stromal tumor, comprising means for detecting and/or analyzing one or more mutations, as defined herein, in any one or both of the marker genes cKIT (GenBank acc. no. NM_000222.2) and PDGFRA (GenBank acc. no. NM_006206.4).

In still another aspect, the present invention relates to the use of one or more mutations, as defined herein, in any one or both of the marker genes cKIT (GenBank acc. no. NM_000222.2) and PDGFRA (GenBank acc. no. NM_006206.4), as a panel of molecular markers for diagnosing and/or monitoring a gastrointestinal stromal tumor or a predisposition to develop a gastrointestinal stromal tumor.

Other embodiments of the present invention will become apparent from the detailed description hereinafter.

(A) Shown are exemplary magnetic resonance images of patient 1 (76 years, female), who is treated with sunitinib. The images were taken in March 2009 (left) and August 2009 (right). The images demonstrate progressive metastases in the liver during therapy (indicated by the arrows). In September 2009, the metastases were treated by high-frequency thermotherapy (HFTT). In October 2009, sunitinib therapy was stopped due to a stroke of patient 1. (B) The images were taken in November 2009 (i.e. after HFTT; left) and May 2010 (right). The metastases in the liver were found to be stable in size but after HFTT a new tumor manifestation became visible (second arrow; left and right).

Figure 2:
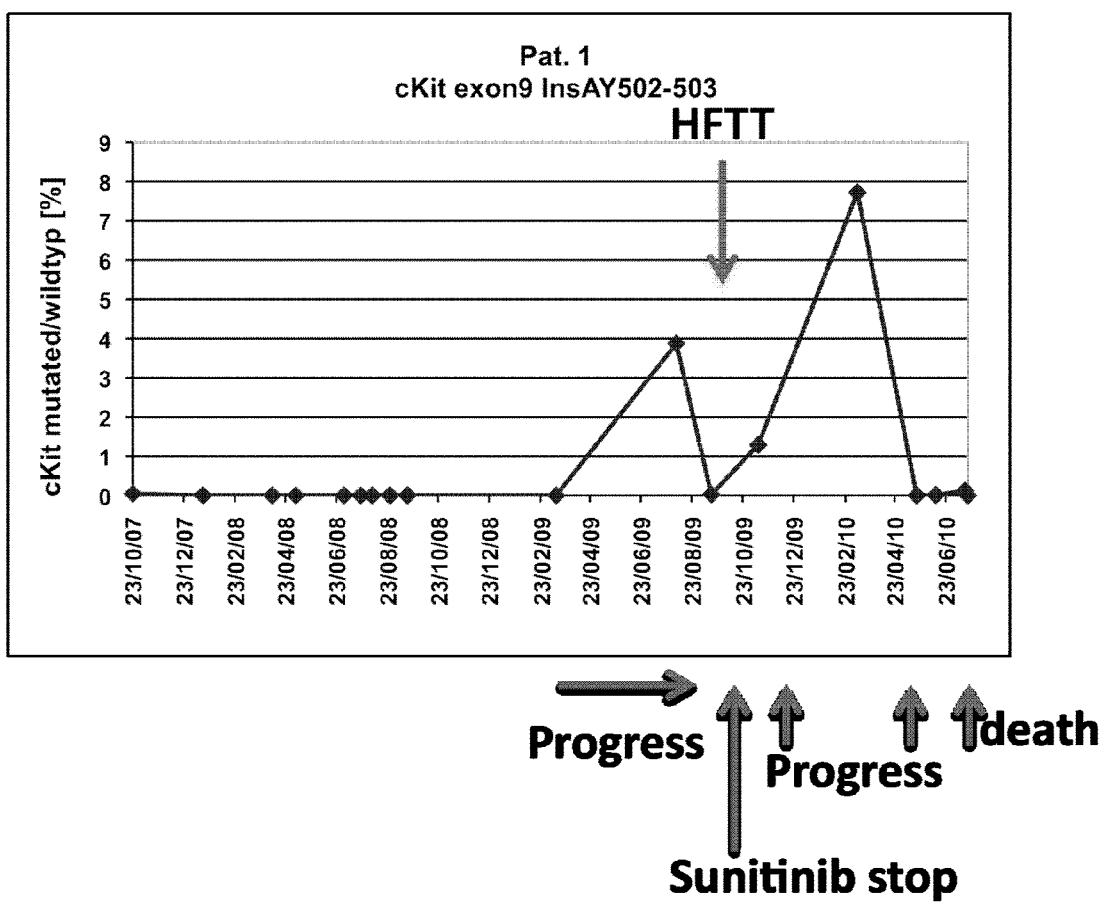

FIG. 2: Patient 1—Correlation of GIST tumor activity with cKIT mutation.

A duplication of the nucleotide sequence GCCTAT corresponding to codons 502-503 of the cKIT marker gene (located in exon 9, encoding the amino acids AY) was detected in the plasma DNA of patient 1. Shown is an analysis of the amount of the mutated cKIT DNA (expressed as allele-specific ration mutated/wild-type cKIT DNA) during sunitinib therapy. The increase in mutated cKIT DNA levels in 2009 parallels the progression of liver metastases. After HFTT, the re-increase in mutated cKIT DNA levels goes along with the new tumor manifestation.

Figure 3:
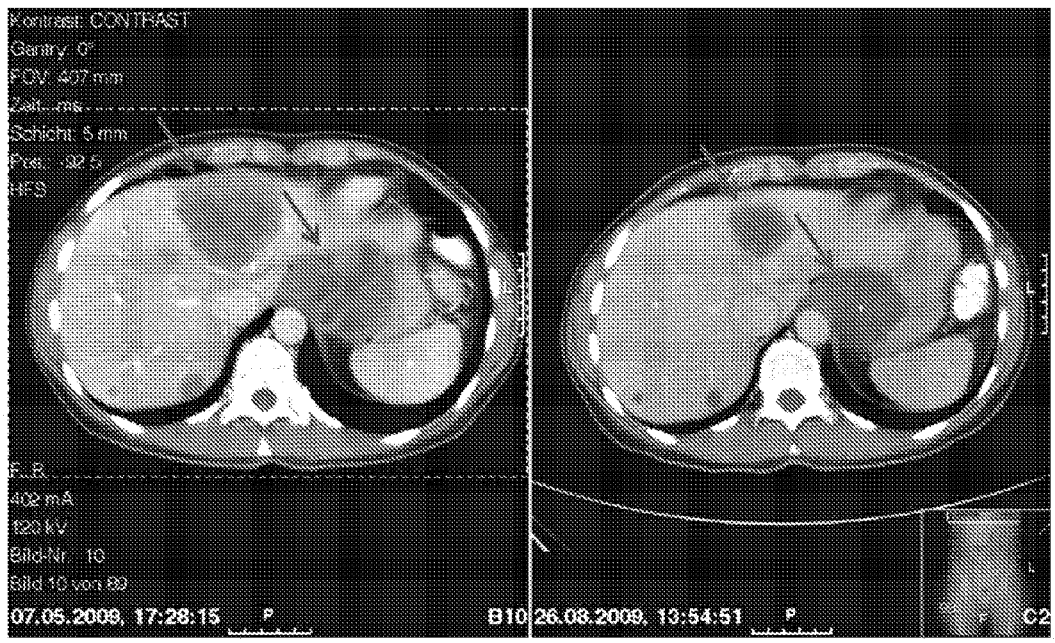
Figure 3:
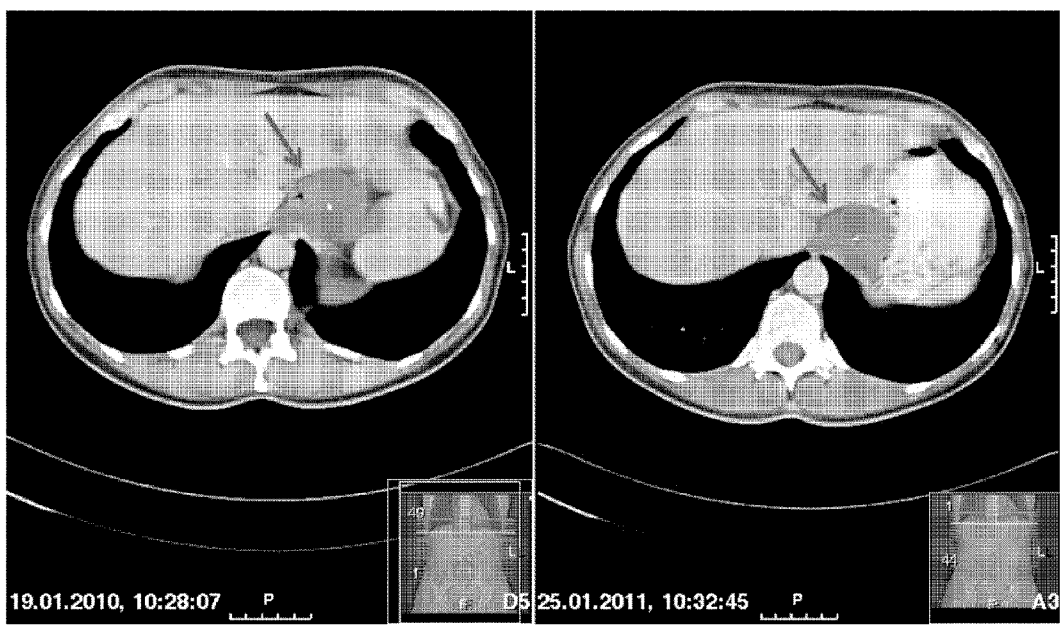

FIG. 3: Patient 2—Monitoring GIST tumor activity.

(A) Shown are exemplary computed tomography images of patient 2 (49 years, female). The images were taken in May 2009 (left; immediately prior to therapy with imatinib) and August 2009 (right; two months after onset of therapy). The images depict a rapid response to therapy, as there is a significant decrease in size, density, and contrast enhancement of liver metastases (indicated by the arrows). (B) In January 2010 (left) and January 2011 (right), a successive further size reduction became visible.

Figure 4:
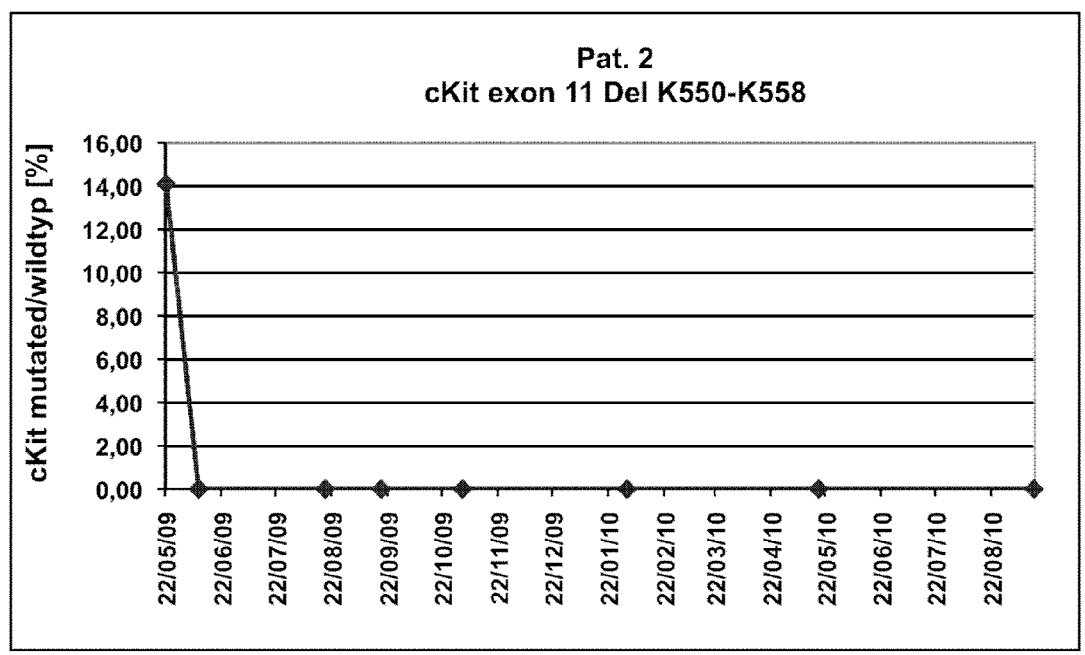
Figure 4:

FIG. 4: Patient 2—Correlation of GIST tumor activity with cKIT mutation.

In the plasma DNA of patient 2, a deletion of the nucleotide sequence AAACCCATGTATGA AGTACAGTGGAAG (SEQ ID NO: 14) corresponding to codons 550-558 of the cKIT marker gene (located in exon 11) was detected. Shown is an analysis of the amount of the mutated cKIT DNA (expressed as allele-specific ration mutated/wild-type cKIT DNA) during imatinib therapy. Notably, only two weeks after onset of imatinib therapy no mutated cKit DNA could be detected in the plasma sample. Hence, there is an excellent correlation between response to therapy, tumor morphology, and presence of a tumor-specific mutated cKIT DNA.

Figure 5:
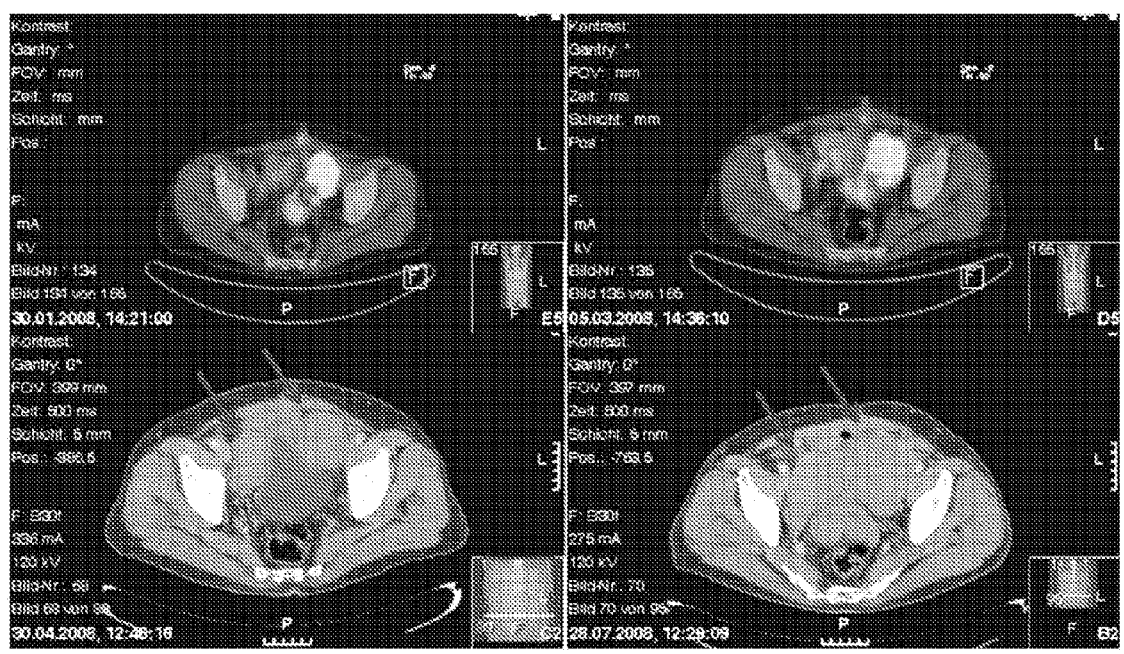

FIG. 5: Patient 3—Monitoring GIST tumor activity.

Shown are exemplary 2-deoxy-2-($^{18}$F)fluoro-D-glucose positron emission-tomography computed tomography (top, left and right) and computed tomography (bottom, left and right) images of patient 3 (65 years, male) having a GIST with stable metastases in the liver and a slow progression of mesenterial metastases. The images were taken in January 2008 (left, top), March 2008 (right, top), April 2008 (left, bottom), and July 2008 (right, bottom). Patient 3 was originally treated with imatinib but developed a resistance. During subsequent therapy with various compounds a further slow progression of mesenterial metastases was observed (indicated by the arrows)

Figure 6:
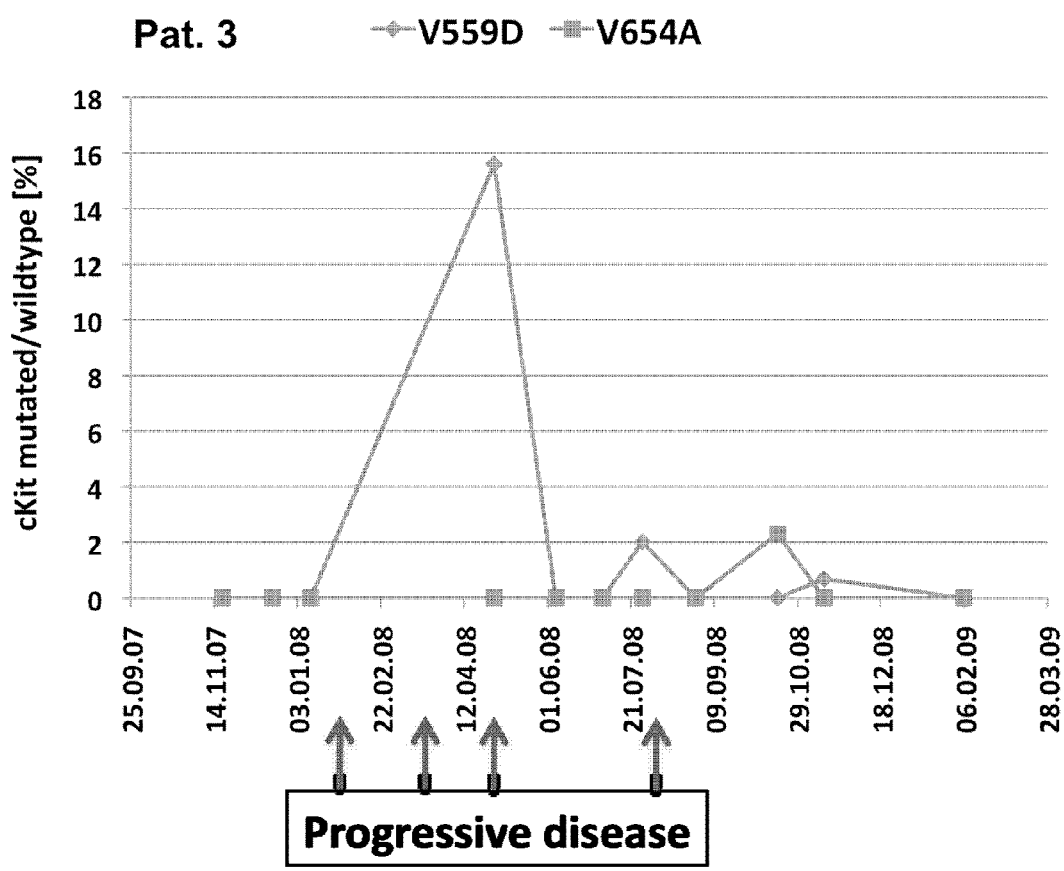

FIG. 6: Patient 3—Correlation of GIST tumor activity with cKIT mutation.

In the plasma DNA of patient 3, a nucleotide substitution GTT→GAT at codon 559 (located in exon 11; encoding the amino acid change VD) was detected. In the context of the resistance towards imatinib a secondary mutation could be found: a nucleotide substitution GTG→GCG at codon 654 (located in exon 13; encoding the amino acid change VA). Shown is an analysis of the amount of the mutated V559D cKIT DNA (blue; expressed as allele-specific ration mutated/wild-type cKIT DNA) and of the amount of the mutated V654A cKIT DNA (red; expressed as allelespecific ration mutated/wild-type cKIT DNA) during therapy. Tumor specific V559D mutated cKIT DNA was identified in three samples, whereas tumor specific V654A-mutated cKIT DNA was identified in one sample.

Figure 7:
Figure 7:
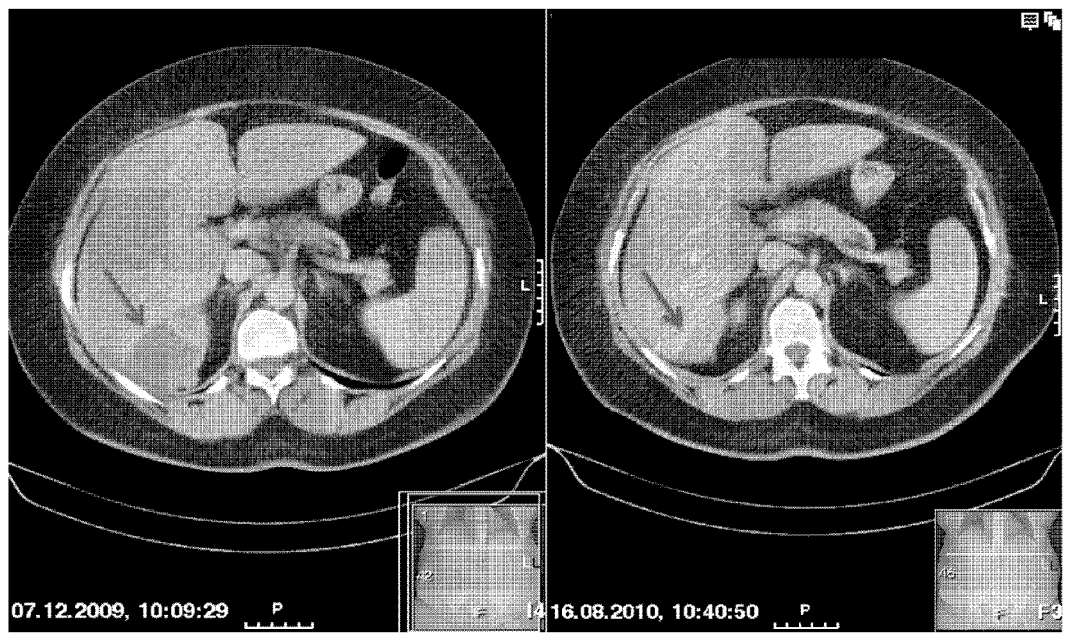

FIG. 7: Patient 4—Monitoring GIST tumor activity.

(A) Shown are exemplary computed tomography images of patient 4 (51 years, female). The images were taken in March 2009 (left) and September 2009 (right). The images demonstrate a relapse with metastases of the liver in September 2009 (right; indicated by the arrow). Starting Patient 4 was treated with imatinib starting in September 2009. (B) The images were taken in December 2009 (left) and August 2010 (right). The metastases in the liver displayed a successive size reduction of about 90% (arrows; left and right).

Figure 8:
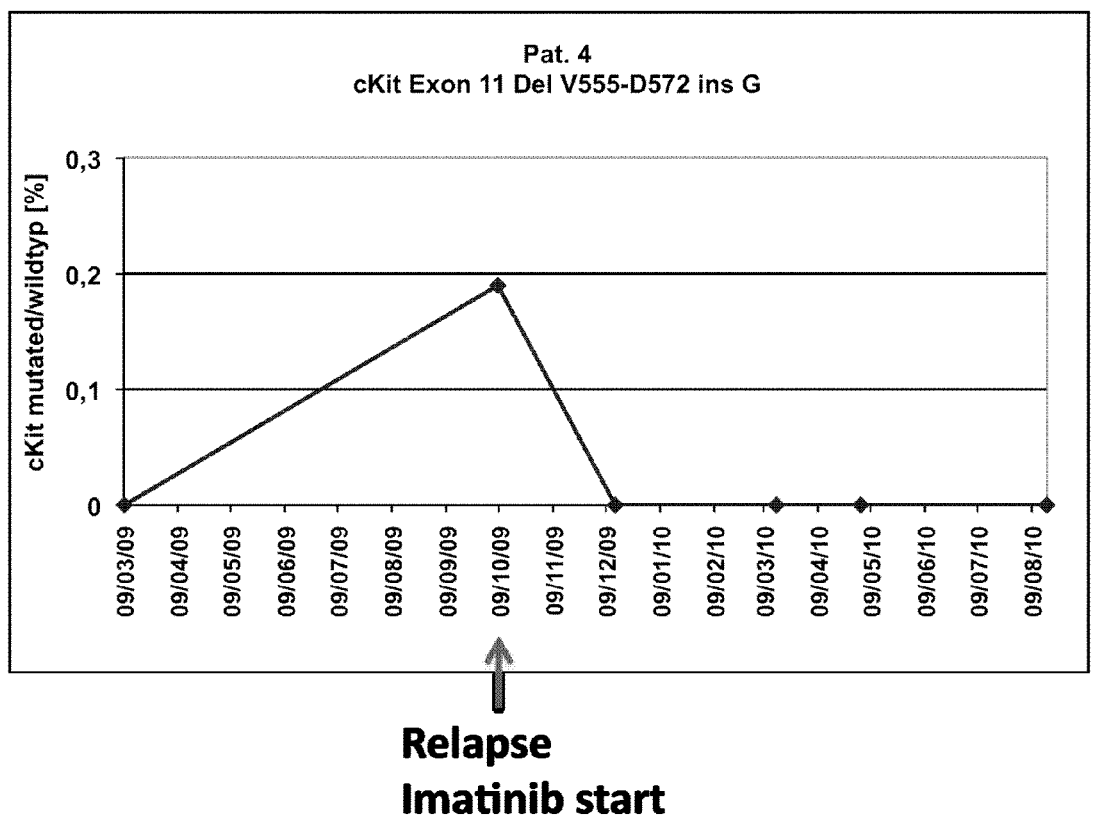

FIG. 8: Patient 4—Correlation of GIST tumor activity with cKIT mutation.

A deletion/insertion of the nucleotide sequence DelA-CAGTGGAAGGTTGTTGAGGAGATAAATG-GAAACAATTATGTTTACATAGACins G (SEQ ID NO: 15) corresponding to codons K550-K558 of the cKIT marker gene (located in exon 11) was detected in the plasma DNA of patient 4. Shown is an analysis of the amount of the mutated cKIT DNA (expressed as allele-specific ratio of mutated/wild-type cKIT DNA) during imatinib therapy. Detection of mutant cKIT DNA in September 2009 parallels the emergence of liver metastases. In plasma samples obtained 6.5 months before relapse and during imatinib treatment with response, mutated cKIT DNA was not detectable.

DETAILED DESCRIPTION OF THE INVENTION

The present invention is based on the unexpected finding that the detection and/or (quantitative) analysis of one or more tumor-specific mutations at the DNA level of the marker genes cKIT and PDGFRA represents a reliable and efficient approach for diagnosing and/or monitoring gastrointestinal stromal tumors or a predisposition of developing such condition. The presence/absence and/or amount of said mutations correlate with morphological data as determined by imaging methods. Hence, these mutations may represent a suitable measure for GIST activity and thus enable the rapid and accurate staging of GISTs as well as the monitoring of tumor progression and responsiveness to a particular therapy. In addition, as the diagnosis is performed on circulating (i.e. cell-free) DNA, e.g., present in plasma samples, the approach of the present invention is also simple, does not require sophisticated equipment, and is cost-effective.

The present invention illustratively described in the following may suitably be practiced in the absence of any element or elements, limitation or limitations, not specifically disclosed herein.

Where the term "comprising" is used in the present description and the claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun, e.g., "a", "an" or "the", this includes a plural of that noun unless specifically stated otherwise.

In case, numerical values are indicated in the context of the present invention the skilled person will understand that the technical effect of the feature in question is ensured within an interval of accuracy, which typically encompasses a deviation of the numerical value given of ±10%, and preferably of ±5%.

Furthermore, the terms first, second, third, (a), (b), (c), and the like, in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used. The following terms or definitions are provided solely to aid in the understanding of the invention. These definitions should not be construed to have a scope less than understood by a person of ordinary skill in the art.

In a first aspect, the present invention relates to an in vitro method for diagnosing and/or monitoring in a subject a gastrointestinal stromal tumor or a predisposition to develop a gastrointestinal stromal tumor, comprising:
detecting and/or analyzing in a test sample derived from the subject one or more mutations at the DNA level in any one or both of the marker genes cKIT (GenBank acc. no. NM_000222.2) and PDGFRA (Gen Bank acc. no. NM_006206.4),
wherein the DNA is circulating DNA; and
wherein the presence of any one of the mutations detected in the test sample is indicative of a gastrointestinal stromal tumor or a predisposition to develop a gastrointestinal stromal tumor in the subject.

The term "tumor", as used herein, generally denotes any type of malignant neoplasm, that is, any morphological and/or physiological alterations (based on genetic re-programming) of target cells exhibiting or having a predisposition to develop characteristics of a tumor as compared to unaffected (healthy) wild-type control cells. Examples of such alterations may relate inter alia to cell size and shape (enlargement or reduction), cell proliferation (increase in cell number), cell differentiation (change in physiological state), apoptosis (programmed cell death) or cell survival.

The term "having a predisposition to develop a tumor", as used herein, denotes any cellular phenotype being indicative for a pre-cancerous state, i.e. an intermediate state in the transformation of a normal cell into a tumor cell. In other words, the term denotes a state of risk of developing a tumor.

The term "gastrointestinal stromal tumor" (also referred to as "GIST"), as used herein, denotes any type of mesenchymal tumors of the gastrointestinal tract (i.e. stomach, small intestine, and esophagus). GISTs represent about 1-3% of all gastrointestinal malignancies. GISTs constitute non-epithelial tumors of the connective tissue (i.e. sarcomas).

Within the present invention, the terms "diagnosing" and "monitoring" are intended to encompass predictions and likelihood analysis (based on both the qualitative and quantitative measurements). The present method is intended to be used clinically in making decisions concerning treatment modalities, including therapeutic intervention, disease staging, and disease monitoring and surveillance. According to the present invention, an intermediate result for examining the condition of a subject may be provided. Such intermediate result may be combined with additional information to assist a physician, nurse, or other practitioner to diagnose that a subject suffers from the disease. Alternatively, the present invention may be used to detect cancerous cells in a subject-derived sample, and provide a doctor with useful information to diagnose that the subject suffers from the disease.

Typically, the method of the present invention is performed as an in vitro method.

A subject to be diagnosed and/or monitored by the present method is a mammal such as a mouse, rat, hamster, rabbit, cat, dog, pig, cow, horse or monkey. Preferably, the subject to be diagnosed is a human.

The test samples to be employed in the present invention are derived (i.e. collected) from the subject to be diagnosed and/or monitored for the presence or the predisposition to develop a GIST (that is, a subject at least suspected to exhibit or develop such condition). The test samples may include body tissues (e.g., biopsies or resections) and fluids, such as blood, sputum, cerebrospinal fluid, and urine. Furthermore, the test samples may contain a single cell, a cell population (i.e. two or more cells) or a cell extract derived from a body tissue. The test samples used in the method of the present invention should generally be collected in a clinically acceptable manner, preferably in a way that nucleic acids or proteins are preserved. The test samples may be used in unpurified form or subjected to any enrichment or purification step(s) prior to use, for example in order to isolate the DNA or the protein fraction comprised in a given sample. The skilled person is well aware of various such purification methods (see, e.g., Sambrook, J., and Russel, D. W. (2001), *Molecular cloning: A laboratory manual* (3rd Ed.) Cold Spring Harbor, N.Y., Cold Spring Harbor Laboratory Press; Ausubel, F. M. et al. (2001) *Current Protocols in Molecular Biology*, Wiley & Sons, Hoboken, N.J., USA).

In specific embodiments, the test sample is a blood sample such as whole blood, plasma, and serum. The term "whole blood", as used herein, refers to blood with all its constituents (i.e. both blood cells and plasma). The term "plasma", as used herein, denotes the blood's liquid medium. The term "serum", as used herein, refers to plasma from which the clotting proteins have been removed. In preferred embodiments, the test sample employed is a plasma sample.

The method of the present invention comprises the detection and/or analysis of one or more mutations in any one or both of the marker genes cKIT and PDGFR. The cKIT gene encodes the stem cell factor receptor (also referred to as mast cell growth factor receptor or CD117), which has tyrosine kinase activity. The PDGFRA gene encodes the platelet derived growth factor receptor-alpha (also referred to as PDGFR2 or CD140A), also exhibiting tyrosine kinase activity.

The two marker genes referred to herein typically represent human sequences known in the art. The respective nucleic acid sequences (encoding the corresponding mRNAs) are deposited in GenBank, the NCBI/NIH genetic sequence database (release 177.0, Apr. 15, 2010; http://www.ncbi.nlm.nih.gov/GenBank/; see also Benson, D. A. et al. (2008) *Nucl. Acids Res.* 36, D25-D30), having the following accession numbers (herein also referred to as "acc. no."):

```
cKIT   (GenBank acc. no. NM_000222.2)(SEQ ID NO: 1)

PDGFRA (GenBank acc. no. NM_006206.4)(SEQ ID NO: 2)
```

The genes or loci may also be designated by synonyms, which are known to the person skilled in the art and can be derived, for example, from the above mentioned database entries. These synonyms are also encompassed by the embodiments of the present invention.

The term "detecting" (or "detection"), as used herein, may be interpreted in the sense of "identifying" at least one mutation present in any of the marker genes, and optionally also in the sense of "selecting" any one or more of the mutations identified for further consideration. The selection may vary, for example, depending on treatment modalities, including therapeutic intervention, diagnostic criteria such as disease stages, and disease monitoring and surveillance in the subject to be treated. The term "analyzing" (or "analysis"), as used herein, may be interpreted as also including a quantitative characterization of at least one mutation present in any of the marker genes (for example, determining the amount of mutated DNA and/or the expression level of the mutated DNA in a given test sample).

The term "mutation", as used herein, refers to any type of nucleic acid alterations known in the art including inter alia a terminal addition of one or more nucleotides, an (internal) insertion of one or more nucleotides (encompassing the duplication of one or more nucleotides), a deletion (i.e. removal) of one or more nucleotides, and a substitution (i.e. change) of one or more nucleotides or combinations thereof. The mutations may represent conservative mutations (i.e. nucleotide mutations that do not result in any changes of the encoded amino acid residues) or non-conservative mutations (i.e. nucleotide mutations that result in changes of the encoded amino acid residues). Within the present invention, the term refers nucleic acid alterations that are (when considered individually or in combination) indicative of a gastrointestinal stromal tumor or a predisposition to develop a gastrointestinal stromal tumor in the subject to be diagnosed.

The term "one or more", as used herein, denotes that the method of the present invention may include the identification of a single mutation present in either of the two marker genes or the detection of at least two mutations. The at least two mutations (i) may all be present in the cKIT gene or (ii) may all be present in the PDGFRA gene or (iii) at least one mutation is present in the cKIT gene and at least one mutation is present in the PDGFRA gene.

The one or more mutations are detected and/or analyzed at the DNA level, that is, by analyzing the nucleic acid sequence of any one or both marker genes for the presence of mutations. However, in some embodiments, the presence of the one or more mutations may further also be detected (as well as quantified) by determining the level of gene expression at the mRNA level and/or at the protein level (for example, if the presence of a mutation results in an up-regulation (gain-of-function) or down-regulation (loss-of-function) of the level of gene expression), or by measuring the functional activity of the encoded protein. The skilled person is well aware of numerous methods for performing such analyses (see, e.g., Sambrook, J., and Russel, D. W. (2001), supra; Ausubel, F. M. et al. (2001) supra). For example, at the DNA level, a direct sequencing approach or various established PCR techniques (e.g., ligation-PCR) may be employed. At the mRNA level, suitable methods include, e.g., Northern blot analyses or RT-PCR. Finally, the protein level may be determined, e.g., by immunochemical methods involving the use of specific antibodies, while protein activity may be measured by enzymatic assays.

In some embodiments, the method further comprises comparing the results obtained in the test sample with those obtained in a control sample. The term "control sample", as used herein, refers to a sample derived from the subject to be diagnosed that is not at least suspected to exhibit GIST activity or to develop such condition. Hence, the term also includes wild-type DNA samples (i.e. DNA not bearing mutations in the cKIT and/or PDGFRA marker genes). Within the present invention, the term "control sample" also refers to reference (control) values derived from databases or published in the scientific literature.

In preferred embodiments, the method of the invention further comprises quantifying the amount of mutated DNA present in the test sample, wherein optionally an elevated amount of mutated DNA in the test sample as compared to the control sample is indicative of gastrointestinal stromal tumor progression.

Such quantification of the amount (concentration) of mutated DNA (and/or its corresponding mRNA) may be performed by various methods well established in the art such as PCR amplification techniques (see, e.g., Sambrook, J., and Russel, D. W. (2001), supra; Ausubel, F. M. et al. (2001) supra).

The DNA amount (and/or the amount of its corresponding mRNA) in the test sample is deemed to be "elevated" when it is increased as compared to the control sample, for example, by 5%, 10%, 20%, 30%, 40%, 50%, 60%, 70%, 80%, 90%, 100% or more than 100% in comparison to a control level. As used herein, such elevated (i.e. increased) amount is considered indicative of tumor progression (i.e. ongoing tumor development). Vice versa, a reduced (i.e. decreased) amount of mutated DNA (and/or the amount of its corresponding mRNA) in the test sample (as compared to the control sample) is considered indicative of tumor regression. An amount of mutated DNA (and/or the amount of its corresponding mRNA) in the test sample that is about the same as in the control sample) is considered indicative of a stalling/stopping of tumor progression.

The DNA used for the detection and/or analysis of the one or more mutations is circulating DNA (herein also referred to as "cell-free DNA"), preferably circulating plasma DNA.

The one or more mutations in any one or both of the marker genes may also be detected and/or analyzed in any other one or more DNA fraction or molecule(s) present in the test sample analyzed, that is, e.g., in cellular DNA (i.e. genomic DNA including nuclear and non-nuclear DNA fractions).

In preferred embodiments, the one or more mutations are located in any one or more of the regions corresponding to the codons 456-508 (located in exon 9; encoding amino acids P456-F508), 549-599 (located in exon 11; encoding amino acids Q549-R599), 642-654 (located in exon 13; encoding K642-V654), 670-709 (located in exon 14; encoding T670-S709), 786-823 (located in exon 17; encoding K786-Y823), and 829 (located in exon 18; encoding amino acid A 829) of the cKIT marker gene (GenBank acc. no. NM_000222.2) and/or in any one or more of the regions corresponding to the codons 478 (located in exon 10; encoding amino acid S478), 561-571 (located in exon 12; encoding amino acids V561-E571), 687 (located in exon 14; encoding amino acid H687), and 824-846 (located in exon 18, encoding amino acids V824-D846) in the PDGFRA marker gene (GenBank acc. no. NM_006206.4). All amino acid residues above are given in the single letter code. Within the present invention, any of the regions indicated above may encompass a single mutation or a combination of at least two mutations. The nucleic acid regions indicated above refer to the respective human marker genes. However, in case, the method of the present invention is performed using test samples of non-human origin the skilled person is well aware of methods for performing nucleic acid sequence comparisons in order to determine the corresponding nucleic acid regions in non-human marker genes. The term "any one or more", as used herein, relates to any one, any subgroup of any two or more (i.e. any two, any three, any four, any five, any six, any seven, any eight, any nine, any ten, and so forth) or all of the regions referred to above.

In particularly preferred embodiments, the one or more mutations in the cKIT marker gene (GenBank acc. no. NM_000222.2) are selected from any one or more from the group consisting of:

a deletion of the nucleotide sequence AAACCCATGTAT-GAAGTACAGTGGAAG (SEQ ID NO: 14) corresponding to codons 550-558 (encoding amino acids K550-K558);

a deletion of the nucleotide sequence CCCATGTATGAA (SEQ ID NO: 16) corresponding to codons 551-554 (encoding amino acids P551-E554);

a deletion of the nucleotide sequence TATGAAGTA-CAGTGGAAG (SEQ ID NO: 17) corresponding to codons 553-558 (encoding amino acids Y553-K558);

a deletion of the nucleotide sequence GAAGTACAGTG-GAAGGTTGTTGAGGAGATA AATGGAAACAAT-TATGTTTACATA (SEQ ID NO: 18) corresponding to codons 554-571 (encoding amino acids E554-1571);

a deletion of the nucleotide sequence TGGAAG corresponding to codons 557-558 (encoding amino acids W557-K558);

a deletion of the nucleotide sequence AAGGTT corresponding to codons 558-559 (encoding amino acids K558-V559);

a deletion of the nucleotide sequence GTTGTT corresponding to codons 559-560 (encoding amino acids V559-V560);

a deletion of the nucleotide sequence GTTGTT corresponding to codons 559-560 (encoding amino acids V559-V560) combined with the nucleotide substitution AAG→AGG at codon 558 (encoding amino acids K→R);

a duplication of the nucleotide sequence GCCTAT corresponding to codons 502-503 (encoding amino acids A502-Y503);

a duplication of the nucleotide sequence ACCCAACA-CAACTTCCTTATGATCACAAA TGGGAGTTTC-CCAGAAACAGGCTGAGTT (SEQ ID NO: 19) corresponding to codons 573-591 (encoding amino acids T573-V591);

an insertion of the nucleotide sequence ACCAACA-CAACTTCCTTATGATCACAAAT GGGAGTTTC-CCAGAAACAGGCTGAGTTTTGG (SEQ ID NO: 10) at codons 573-592 (encoding amino acids P573-G592);

an insertion of the nucleotide sequence TCCCAACA-CAACTTCCTTATGATCACAA ATGGGAGTTTC-CCA (SEQ ID NO: 12) at codon 586;

the nucleotide substitution TGG→CGG at codon 557 (encoding amino acids W→R);

the nucleotide substitution TGG→GGG at codon 557 (encoding amino acids W→G);

the nucleotide substitution AAG→CCG at codon 558 (encoding amino acids K→P);

the nucleotide substitution AAG→AAC/T at codon 558 (encoding amino acids K→N);

the nucleotide substitution AAG→ACG at codon 558 (encoding amino acids K→T);

the nucleotide substitution AAG→AGG at codon 558 (encoding amino acids K→R);

the nucleotide substitution GTT→GAT at codon 559 (encoding amino acids V→D);

the nucleotide substitution GTT→GCT at codon 559 (encoding amino acids V→A);

the nucleotide substitution GTT→GGT at codon 559 (encoding amino acids V→G);

the nucleotide substitution GTT→GANG at codon 559 (encoding amino acids V→E);

the nucleotide substitution GTT→GAT at codon 560 (encoding amino acids V→D);

the nucleotide substitution GTT→GANG at codon 560 (encoding amino acids V→E);

the nucleotide substitution GTT→GGT at codon 560 (encoding amino acids V→G);

the nucleotide substitution AAA→GAA at codon 642 (encoding amino acids K→E);

the nucleotide substitution GTG→GCG at codon 654 (encoding amino acids V→A);

the nucleotide substitution GAC→GTC at codon 816 (encoding amino acids D→V); and the nucleotide substitution GAC→TTC at codon 816 (encoding amino acids D→F).

In other particularly preferred embodiments, the one or more mutations in the cKIT marker gene (GenBank acc. no. NM_000222.2) are selected from any one or more from the group consisting of:

a deletion of the nucleotide sequence AAACCCATGTATGAAGTACAGTGGAAG (SEQ ID NO: 14) corresponding to codons 550-558 (encoding amino acids K550-K558);

a deletion of the nucleotide sequence CCCATGTATGAA (SEQ ID NO: 16) corresponding to codons 551-554 (encoding amino acids P551-E554);

a deletion of the nucleotide sequence GTATGAAGTACAGTGGAAGGTSEQ ID NO: 20) corresponding to codons 552-559 (encoding amino acids P552-E559);

a deletion of the nucleotide sequence TGAAGTACAGTGGAAGGTTGTTGAG GAG ATAAATGGAAACAATTATGTTTACATAGA (SEQ ID NO: 21) corresponding to codons 553-572 (encoding amino acids Y553-D572);

a deletion of the nucleotide sequence TATGAAGTACAGTGGAAG (SEQ ID NO: 17) corresponding to codons 553-558 (encoding amino acids Y553-K558);

a deletion of the nucleotide sequence GAAGTACAGTGGAAGGTTGTTGAGGAGATA AATGGAAACAATTATGTTTACATA (SEQ ID NO: 18) corresponding to codons 554-571 (encoding amino acids E554-1571);

a deletion of the nucleotide sequence TGGAAG corresponding to codons 557-558 (encoding amino acids W557-K558);

a deletion of the nucleotide sequence AAGGTT corresponding to codons 558-559 (encoding amino acids K558-V559);

a deletion of the nucleotide sequence GTTGTT corresponding to codons 559-560 (encoding amino acids V559-V560);

a deletion of the nucleotide sequence TGAAGTACAGTGGAAGGTTGTTGA (SEQ ID NO: 22) corresponding to codons 554-561 (encoding amino acids E554-E561) combined with the nucleotide insertion CTT;

a deletion of the nucleotide sequence ACAGTGGAAGGTTGTTGAGGAGATAAATG GAAACAATTATGTTTACATAGAC (SEQ ID NO: 15) corresponding to codons 555-572 (encoding amino acids V555-D572) combined with the nucleotide insertion G;

a deletion of the nucleotide sequence GTTGTT corresponding to codons 559-560 (encoding amino acids V559-V560) combined with the nucleotide substitution AAG→AGG at codon 558 (encoding amino acids K→R);

a deletion of the nucleotide sequence GTTGAGGAGATAAATGGAAACAATTATGTTT ACATAGACCCAACACAACTTCCTTAT (SEQ ID NO: 23) corresponding to codons 560-578 (encoding amino acids V560-Y578);

a deletion of the nucleotide sequence ACACAACTTCCTTATGATCAC (SEQ ID NO: 24) corresponding to codons 574-580 (encoding amino acids T574-H580);

a deletion of the nucleotide sequence GAT corresponding to codon 578 (encoding amino acid D578);

a duplication of the nucleotide sequence GCCTAT corresponding to codons 502-503 (encoding amino acids A502-Y503);

a duplication of the nucleotide sequence ACCCAACACAACTTCCTTATGATCACAAA TGGGAGTTTCCCAGAAACAGGCTGAGTT (SEQ ID NO: 19) corresponding to codons 573-591 (encoding amino acids T573-V591);

an insertion of the nucleotide sequence ACCAACACAACTTCCTTATGATCACAAAT GGGAGTTTCCCAGAAACAGGCTGAGTTTTGG (SEQ ID NO: 10) at codons 573-592 (encoding amino acids P573-G592);

an insertion of the nucleotide sequence GCAAACAACACAACTTCCTTATGATCACAA ATGGGAGTTTCC (SEQ ID NO: 11) at codon 585;

an insertion of the nucleotide sequence TCCCAACACAACTTCCTTATGATCACAA ATGGGAGTTTCCCA (SEQ ID NO: 12) at codon 586;

an insertion of the nucleotide sequence ACAACTTCCTTATGATCACAAATGGGAG TTTCCCAGAAACAGGCT (SEQ ID NO: 13) at codon 589;

the nucleotide substitution TGG→CGG at codon 557 (encoding amino acids W→R);

the nucleotide substitution TGG→GGG at codon 557 (encoding amino acids W→G);

the nucleotide substitution AAG→CCG at codon 558 (encoding amino acids K→P);

the nucleotide substitution AAG→AAC/T at codon 558 (encoding amino acids K→N);

the nucleotide substitution AAG→ACG at codon 558 (encoding amino acids K→T);

the nucleotide substitution AAG→AGG at codon 558 (encoding amino acids K→R);

the nucleotide substitution GTT→GAT at codon 559 (encoding amino acids V→D);

the nucleotide substitution GTT→GCT at codon 559 (encoding amino acids V→A);

the nucleotide substitution GTT→GGT at codon 559 (encoding amino acids V→G);

the nucleotide substitution GTT→GANG at codon 559 (encoding amino acids V→E);

the nucleotide substitution GTT→GAT at codon 560 (encoding amino acids V→D);

the nucleotide substitution GTT→GANG at codon 560 (encoding amino acids V→E);

the nucleotide substitution GTT→GGT at codon 560 (encoding amino acids V→G);

the nucleotide substitution AAA→GAA at codon 642 (encoding amino acids K→E);

the nucleotide substitution GTG→GCG at codon 654 (encoding amino acids V→A);

the nucleotide substitution GAC→GTC at codon 816 (encoding amino acids D→V); and the nucleotide substitution GAC→TTC at codon 816 (encoding amino acids D→F).

In further particularly preferred embodiments, the one or more mutations in the PDGFRA marker gene (GenBank acc. no. NM_006206.4) comprise the nucleotide substitution GAC→GTC at codon 842 (encoding amino acids D→N).

In yet other particularly preferred embodiments, the one or more mutations in the PDGFRA marker gene (GenBank acc. no. NM_006206.4) are selected from any one or more from the group consisting of: the nucleotide substitution GAC→GTC at codon 842 (encoding amino acids D→V); and a deletion of the nucleotide sequence corresponding to codons 542-546 (CATCATGCATGA).

All these particular mutations of the cKIT and PDGFRA marker genes referred to above are well known in the art and published inter alia in: Hirota, S. et al. (1998) *Science* 279, 577-580; Rubin, B. P. et al. (2001) *Cancer Res.* 61, 8118-

8121; Hirota, S. et al. (2003) *Gastroenterology* 125, 660-667; Corless, C. L. et al. (2005) *J. Clin. Oncol.* 23, 5357-5364; and Corless, C. L. and Heinrich, M. C. (2008), supra.

Again, the nucleic acid regions indicated above refer to the respective human marker genes. However, in case, the method of the present invention is performed using test samples of non-human origin the skilled person is well aware of methods for performing nucleic acid sequence comparisons in order to determine the corresponding nucleic acid regions in non-human marker genes. The terms "one or more" or "any one or more", as used herein, relate to any one, any subgroup of any two or more (i.e. any two, any three, any four, any five, any six, any seven, any eight, any nine, any ten, and so forth) or all of the particular mutations referred to above.

In further specific embodiments, the detection and/or (quantitative) analysis of the one or more mutations is performed by an allele-specific method (i.e. by directly comparing mutated and wild-type DNA fractions or samples), preferably by allele-specific PCR techniques such as, for example, ligation-PCR (cf. the detailed description in the experimental section below). Such allele-specific PCR techniques are known in the art (see, e.g., Sambrook, J., and Russel, D. W. (2001), supra; Ausubel, F. M. et al. (2001) supra).

In some other embodiments, the method is performed in a multiplex format. The term "multiplex format", as used herein, refers to the parallel detection analysis of two or more mutations present in the same test sample within a single assay (for example, depending on the detection method employed by using separate reaction containers for each of the mutations concerned) as well as two the parallel analysis of two or more test samples in parallel (wherein the one or more mutations analyzed in the two or more test samples may be the same or different). The term also includes high-throughput analyses, for example by employing microarray technology.

In another aspect, the present invention relates to a kit-of-parts for diagnosing and/or monitoring a gastrointestinal stromal tumor or a predisposition to develop a gastrointestinal stromal tumor, comprising
means for detecting and/or analyzing one or more mutations, as defined herein above, in any one or both of the marker genes cKIT (GenBank acc. no. NM_000222.2) and PDG-FRA (GenBank acc. no. NM_006206.4).

Means for detecting and/or analyzing one or more mutations (at the DNA level) in the two marker genes employed may include inter alia one or more specific DNA oligonucleotides to be employed as PCR primers or probe molecules for amplifying any particular regions of the respective marker genes bearing such tumor-specific mutations or for performing sequence analyses. The kit-of-part according to the invention may further comprise reagents for performing said assays such as enzymes (e.g., DNA polymerases) as well as for isolating and/or purifying a test sample (and a control sample) to be analyzed (e.g., reagents for DNA purification).

The various components of the kit may be packaged in one or more containers such as one or more vials. For example, each component comprised in the kit may be packaged in a separate container.

The components of the kit may be provided in lyophilized or dry form or dissolved in a suitable buffer such as phosphate-buffered saline or Tris/EDTA (TE)-buffer. The kit may also comprise additional reagents including inter alia preservatives, buffers for storage and/or reconstitution of the above-referenced components, washing solutions, and the like. These reagents may be provided in combination with one or more of the components indicated above, that is, in the same container (e.g. a DNA oligonucleotide dissolved in an appropriate buffer). Alternatively, at least some of these additional reagents may be provided in separate containers.

In another aspect, the present invention relates to the use of one or more mutations, as defined herein above, in any one or both of the marker genes cKIT (GenBank acc. no. NM_000222.2) and PDGFRA (GenBank acc. no. NM_006206.4), as a panel of molecular markers for diagnosing and/or monitoring a gastrointestinal stromal tumor or a predisposition to develop a gastrointestinal stromal tumor.

Within the present invention, the term "use" is to be understood as referring to both the qualitative and quantitative information obtained by performing the methods defined herein above (i.e. the "mutation status" of the marker genes in a given test sample including the identification of any mutations as well as the determination of the amount of mutated DNA). In other words, such "mutation status" is used as a "signature" for the diagnosis and/or staging of a GIST and/or for the monitoring of tumor progression or responsiveness to a given therapy.

The invention is further described by the figures and the following examples, which are solely for the purpose of illustrating specific embodiments of this invention, and are not to be construed as limiting the scope of the invention in any way.

EXAMPLES

Example 1

Ligation-PCR

The detection of tumor-specific mutant DNA fragments in plasma samples requires experimental methods having both high sensitivity and specificity for the tumor-specific DNA as the latter fraction sometimes represents less than 0.01% of the total DNA. Within the present invention, ligation-PCR was employed in this respect as an exemplary method.

1.1 Design of the Oligonucleotides

Because free plasma DNA results from fragmentation of genomic DNA intron-exon sequences of the target gene (to be amplified) are used to design the respective oligonucleotides. The ligation PCR technique requires two probe pairs per assay. The first pair is complementary to the wild type sequence and the second pair spans the mutated region. Primers and nested primers for both wild type and mutated allele are flanking the probes. The melting temperature of the probes should be adjusted to 65° C. (+1-2° C.) in order to have similar melting temperatures for hybridization and ligation reaction. The high temperature (60-65° C.) during the ligation reaction results in the annealing and subsequent fusion of the probes only if there is a perfect match at the mutation site. Furthermore, ligation requires a 5'-phosphate modification of probe 2. The 5'-end of probe 1 and the 3'-end of probe 2 encompass two synthetic sequences in order to introduce a PCR primer binding sites. These sequences are universal for any mutation specific assay. In case, probes 1 and 2 are ligated, the probes and primers for the synthetic outside sequences are used for amplification using real time PCR technique.

Probes Specific for the Mutated Allele:

Probe 1 of the mutated region encompasses the mutation at the 3'-end, while the 5'-end of probe 2 is complementary to the neighboring base in 5' direction.

Probes Specific for the Wild Type Allele:

A non-mutated exon region is used for the design of probes complementary to the wild type sequence that are necessary for the subsequent quantification of non-mutated DNA. Since plasma DNA contains only short DNA fragments, the mutation- and wild type probes should be designed as close as possible to generate a short PCR product.

Amplification Primers:

The amplification primers must flank both wild type and mutation specific probes.

In order to determine the optimal annealing temperature for a given PCR reaction gradient PCR annealing temperatures in the range between 48-72° C. were used to optimize each reaction assay.

1.2 Extraction of Free Circulating DNA in Plasma and Serum

Blood plasma or serum was separated from the blood cells by centrifugation. Aliquots may were stored at −20° C. Free circulating DNA of 1-5 ml of plasma was extracted by using the QIAamp Circulating Nucleic Acid Kit or the QIAamp DNA Blood Mini Kit (both purchased from QIAGEN GmbH, Hilden, Germany) according to the protocol of the manufacturer.

1.3 Allele-Specific Hybridization

Stringent hybridizations of probes complementary to the wild type and mutated allele sequence were employed in different reaction tubes. Known mutation positive tumor DNA, plasmids or synthetic oligonucleotides were used as positive controls. Genomic wild type DNA served as a negative control. The PCR products were usually diluted 1:20.000 (range 1:10.000 to 1:40.000) in water. In order to remove any secondary structures of the DNA, a denaturation step (5 min, 98° C.) of 5 µl diluted DNA followed by cooling to 4° C. was performed. Probes 1 and 2 in Salsa MLPA buffer (Lig-5a, MRC-Holland, Amsterdam, The Netherlands) was added to the DNA dilution in a final concentration of 0.25 nM. After a short denaturation step (1 min, 95° C.) hybridization of the DNA/probe mix was performed over night (16 hours, 60-65° C.).

1.4 Ligation Reaction

Ligase-65 mix (Lig-5a, MRC-Holland, Amsterdam, The Netherlands; per sample 25 µl aqua dest., 1 µl Ligase-65, 3 µl Ligase Puffer A and 3 µl Ligase-65 Puffer B) was pre-incubated at 60-65° C. (5-10 min) and added to the DNA/probe mix at 60-65° C. The ligation reaction was stopped after 5 min, followed by a short denaturation step (5 min, 98° C.). Subsequently, the samples were cooled to 4° C.

1.5 Real Time-PCR

5 µl of the ligated PCR product were added to 20 µl SYBR Green PCR mix (per sample 7.4 µl aqua dest., 0.05 µl universal primer-for (100 µM), 0.05 µl universal primer-rev (100 µM) and 12.5 µl Quantitect SYBR Green PCR Kit 2×; QIAGEN GmbH, Hilden, Germany). The TaqMan-PCR application was performed with the conditions for universal primer according to the manufacturer.

1.6 Analysis of the Results of the Real Time-PCR

The ct (cycle threshold) values of the wild type amplification should not exceed ct25, and the melting temperatures (Tm) of all samples should be identical (+/−0.8° C.). The ct values of the samples with mutated probes depend on the yield of mutated allele in the sample. In a typical PCR run, the Tm of the negative control should be higher than ct 30 and represent the cross reactivity of the probes. The delta ct method was used to calculate the relative percentage of the mutated allele relative to the wild-type allele: $2^{-(\Delta ct)} * 100$. Ct values of mutation and wild type reaction will be directly compared to determine mutated allele in the wild type background (minus cross reactivity) in %.

1.7 Specific Example: Design of a Ligation PCR Assay for the Detection of the cKIT Mutation V559D in the Patient 3 (Cf. Below)

Probes for mutated region (mutation-specific sequence region shown in capitals, mutated allele shown in bold and underlined):

```
Probes for mutated region (mutation-specific sequence region shown
in capitals, mutated allele shown in bold and underlined):
cKitV559D_1                                                              (SEQ ID NO: 3)
5'-gggttccctaagggttggaCCCATGTATGAAGTACAGTGGAAGGA-3' cKitV559D_2 (5'phosphate)                                                (SEQ ID NO: 4)
5'-TGTTGAGGAGATAAATGGAAACAATTATGTTTACATggcgtctagattggatcttgctggcac-3'

Probes for wild type region (wild-type - specific sequence region
shown in capitals):
cKit-wt_1                                                                (SEQ ID NO: 5)
5'-gggttccctaagggttggaCGTAGCTGGCATGATGTGCATTATTGT-3' cKit-wt_2 (5'phosphate)                                                  (SEQ ID NO: 6)
5'-GATGATTCTGACCTACAAATATTTACAGGTAACCATTctagattggatcttgctggcac-3'

Amplification primers:
cKit_f                                                                   (SEQ ID NO: 7)
5'-CACCCTGTTCACTCCTTTGCTG-3' cKit_r1 (Nested-Primer)                                                  (SEQ ID NO: 8)
5'-CCCATTTGTGATCATAAGGAAGTTGTG-3' cKit_r2                                                                  (SEQ ID NO: 9)
5'-AAAACTCAGCCTGTTTCTGGGAAACT-3'
```

Amplification using the primers cKit_f/cKit_r2 results in a PCR product of 308 bp in length, whereas amplification using the primers cKit_f/cKit_r1 results in a PCR product of 282 bp in length.

Example 2

Results 2.1 Analysis of Patient 1

Figure 1:
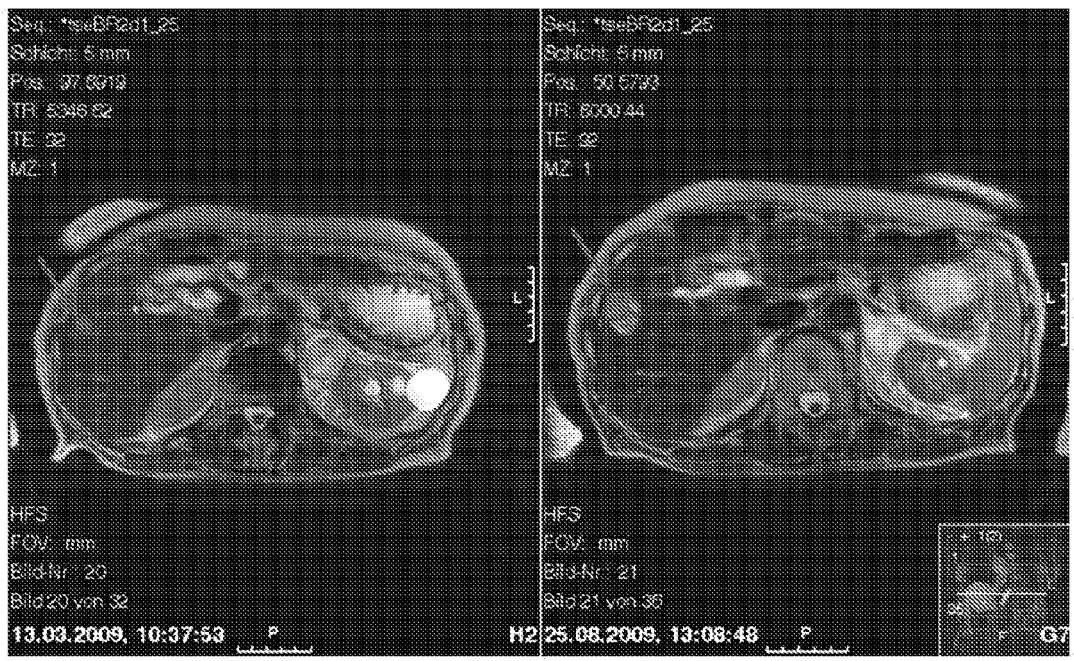
FIG. 1: Patient 1—Monitoring GIST tumor activity.
Figure 1:
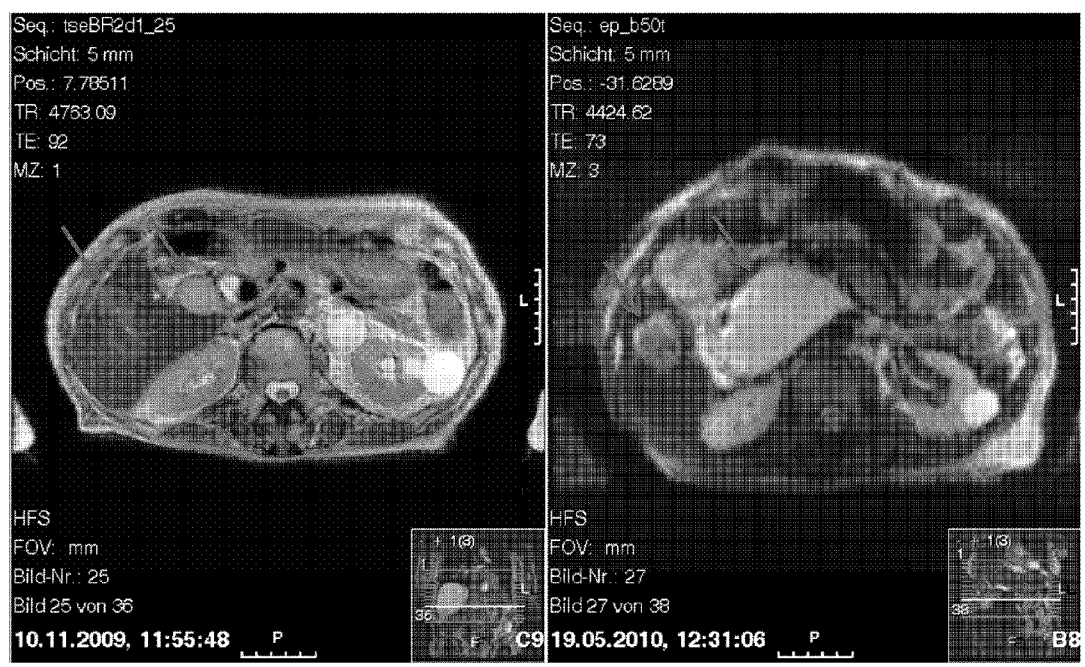

Patient 1 is a 76 years old female having a GIST with hepatic metastases. Patient 1 is treated with sunitinib. FIG. 1 shows exemplary magnetic resonance (MR) images monitoring GIST tumor activity. The images in FIG. 1(A) were taken in March 2009 (left) and August 2009 (right) and demonstrate progressive metastases in the liver during therapy (indicated by the arrows; about a 150% increase in size). In September 2009, the metastases were treated by high-frequency thermotherapy (HFTT). In October 2009, sunitinib therapy was stopped due to a stroke of patient 1 (data not shown). The MR images in FIG. 1(B) were taken in November 2009 (i.e. after HTFF, left) and May 2010 (right). The metastases in the liver were found to be stable in size (only about 5% increase; first arrow, left and right) but after HFTT a new tumor manifestation became visible that increased in size (second arrow; left and right).

A duplication of the nucleotide sequence GCCTAT corresponding to codons 502-503 of the cKIT marker gene (located in exon 9, encoding the amino acids AY) was detected in the plasma DNA of patient 1. FIG. 2 depicts an analysis of the amount of the mutated cKIT DNA (expressed as allele-specific ratio of mutated/wild-type cKIT DNA) during sunitinib therapy. The increase in mutated cKIT DNA levels in 2009 parallels the progression of liver metastases. After HFTT, the re-increase in mutated cKIT DNA levels appears to parallel with the new tumor manifestation.

2.2 Analysis of Patient 2

Patient 2 is a 49 years old female having a GIST with hepatic metastases in the stomach. The computed tomography (CT) images in FIG. 3(A) were taken in May 2009 (left) immediately prior to the onset of a therapy with imatinib and in August 2009 (right), that is, approximately two months after onset of therapy. The images depict a rapid response to therapy, as there is a significant decrease in size, density, and contrast enhancement of liver metastases (indicated by the arrows) as well as of the primary tumor (about a 35% reduction in size). The computed tomography (CT) images in FIG. 3(B) were taken in January 2010 (left) and January 2011 (right), respectively, where a successive further size reduction became visible (about a further 30% reduction in size).

In the plasma DNA of patient 2, a deletion of the nucleotide sequence AAACCCATGTATGAAGTACAGTGGAAG (SEQ ID NO: 14) corresponding to codons 550-558 of the cKIT marker gene (located in exon 11) was detected. FIG. 4 depicts an analysis of the amount of the mutated cKIT DNA (expressed as allele-specific ration mutated/wild-type cKIT DNA) during imatinib therapy. Notably, only two weeks after onset of imatinib therapy no mutated cKit DNA could be detected in the plasma sample. Hence, there is an excellent correlation between response to therapy, tumor morphology, and presence of a tumor-specific mutated cKIT DNA.

2.3 Analysis of Patient 3

Patient 3 is a 65 years old male having a GIST with stable metastases in the liver and a slow progression of mesenterial metastases. The 2-deoxy-2-($^{18}$F)fluoro-D-glucose positron emission-tomography computed tomography (FDG-PET-CT; top, left and right) and computed tomography (bottom, left and right) images shown in FIG. 5 were taken in January 2008 (left, top), March 2008 (right, top), April 2008 (left, bottom), and July 2008 (right, bottom). Patient 3 was originally treated with imatinib but developed a resistance. During subsequent therapy with various compounds a further slow progression of mesenterial metastases was observed (indicated by the arrows; about 10% in size).

In the plasma DNA of patient 3, a nucleotide substitution GTT→GAT at codon 559 (located in exon 11; encoding the amino acid change V→D) was detected. In the context of the resistance towards imatinib a secondary mutation could be found: a nucleotide substitution GTG→GCG at codon 654 (located in exon 13; encoding the amino acid change V→A). FIG. 6 shows an analysis of the amount of the mutated V559D cKIT DNA (expressed as allele-specific ration mutated/wild-type cKIT DNA) during therapy. Tumor specific V559D-mutated cKIT DNA was identified in three samples, whereas tumor specific V654A-mutated cKIT DNA was identified in one sample.

These data show that the amount of tumor-specific DNA present in the respective plasma samples correlate with disease progression during therapy.

2.4 Analysis of Patient 4

Patient 4 is a 51 years old female having an ileum GIST that was treated with ileum segment resection in 2005 followed by three years of adjuvant imatinib treatment. The computed tomography images in FIG. 7(A) were taken in March 2009 (left) and September 2009 (right), respectively. In March 2009, the images did not show evidence of relapse. In contrast, the image staken in September 2009 demonstrated hepatic metastases (arrow in FIG. 7(A); (left). From October 2009, Patient 4 was treated with imatinib. The images shown in FIG. 7(B) were taken in December 2009 (left) and August 2010 (right), and show response to treatment with a successive size reduction of hepatic metastases (about a 90% reduction in size).

A deletion/insertion of the nucleotide sequence DelA-CAGTGGAAGGTTGTTGAGGAGATAA ATGGAAA-CAATTATGTTTACATAGACinsG (SEQ ID NO: 15) corresponding to codons K550-K558 of the cKIT marker gene (located in exon 11) was detected in the plasma DNA of patient 4. FIG. 8 depicts an analysis of the amount of the mutated cKIT DNA (expressed as allele-specific ratio of mutated/wild-type cKIT DNA) before and during imatinib therapy. Detection of mutated cKIT DNA in October 2009 parallels the relapse with liver metastases. No mutated cKit DNA could be detected in plasma samples obtained 6.5 months before relapse and in plasma samples taken after the onset of imatinib therapy. Hence, there is an excellent correlation between response to therapy, tumor morphology, and presence of a tumor-specific mutated cKIT DNA.

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. In vitro method for diagnosing and/or monitoring in a subject a gastrointestinal stromal tumor, the method comprising:
    detecting in a test sample derived from the subject one or more tumor specific mutations at the DNA level in any one or both of the marker genes cKIT (GenBank acc. no. NM_000222.2) and PDGFRA (GenBank acc. no. NM_006206.4); and
    determining the amount of tumor specific mutated DNA, wherein the amount of tumor specific mutated DNA is determined by directly comparing tumor specific mutated and wild-type DNA fractions;
    wherein the DNA is circulating DNA;
    wherein the presence of any one of the tumor specific mutations detected in the test sample is indicative of a gastrointestinal stromal tumor in the subject; and
    wherein an elevated amount of tumor specific mutated DNA is indicative of gastrointestinal stromal tumor progression.

2. The method of claim 1, wherein the test sample is a blood sample.

3. The method of claim 2, wherein the blood sample is a plasma sample.

4. The method of claim 1, wherein the one or more tumor specific mutations are located in any one or more of the regions corresponding to the codons 456-508, 549-599, 642-654, 670-709, 786-823, and 829 of the cKIT marker gene (GenBank acc. no. NM_000222.2) and/or in any one or more of the regions corresponding to the codons 478, 561-571, 687, and 824-846 in the PDGFRA marker gene (GenBank acc. no. NM_006206.4).

5. The method of claim 4, wherein the one or more tumor specific mutations in the cKIT marker gene (GenBank acc. no. NM_000222.2) are selected from the group consisting of:
    a deletion of any one or more of the nucleotide sequences corresponding to codons 550-558, 551-554, 552-559, 553-572, 553-558, 554-571, 557-558, 558-559, and 559-560, 560-578, 574-580, 578;
    a deletion of any one or more of the nucleotide sequences corresponding to codons 554-561 combined with nucleotide insertion CTT;
    a deletion of any one or more of the nucleotide sequences corresponding to codons 555-572 combined with the nucleotide insertion G;
    a deletion of the nucleotide sequence corresponding to codons 559-560 combined with the nucleotide substitution AAG→AGC at codon 558;
    a duplication of any one or more of the nucleotide sequences corresponding to codons 502-503 and 573-591;
    an insertion of the nucleotide sequence ACCAACA-CAACTTCCTTATGATCACAAATGG-GAGTTTCCCAGAAACAGGCTGAGTT TTGG [SEQ ID NO:10] at codons 573-592;
    an insertion of the nucleotide sequence GCAAACAACA-CAACTTCCTTATGATCACAAATGGGAGTTTCC [SEQ ID NO:11] at codon 585;
    an insertion of the nucleotide sequence TCCCAACA-CAACTTCCTTATGATCACAAATGG-GAGTTTCCCA [SEQ ID NO:12] at codon 586;
    an insertion of the nucleotide sequence ACAACTTCCT-TATGATCACAAATGGGAGTTTCCCA-GAAACAGGCT [SEQ ID NO:13] at codon 589; and
    any one or more of the nucleotide substitutions TGG→CGG and TGG→GGG at codon 557; AAG→CCG, AAG→AAC/T, AAG→ACG, and AAG→AGG at codon 558; GTT→GAT, GTT→GCT, GTT→GGT, and GTT→GAA/G at codon 559; GTT→GAT, GTT→GANG, and GTT→GGT at codon 560; AAA→GAA at codon 642; GTG→GCG at codon 654; and GAC→GTC and GAC→TTC at codon 816.

6. The method of claim 4, wherein the one or more tumor specific mutations in the PDGFRA marker gene (GenBank acc. no. NM_006206.4) are selected from the group consisting of: the nucleotide substitution GAC→GTC at codon 842; and a deletion of the nucleotide sequence corresponding to codons 542-546.

7. The method of claim 1, wherein the detection and/or analysis of the one or more tumor specific mutations is performed by an allele-specific PCR technique.

8. The method of claim 1, wherein the method is performed in a multiplex format.

9. The method of claim 1, further comprising providing a kit-of-parts for diagnosing or monitoring a gastrointestinal stromal tumor, wherein the kit-of-parts comprises one or more components for detecting and determining the amount of tumor specific mutated DNA comprising one or more tumor specific mutations in any one or both of the marker genes cKIT (GenBank acc. no. NM_000222.2) and PDG-FRA (GenBank acc. no. NM_006206.4), and instructions for detecting and determining the amount of tumor specific mutated DNA.

10. The method of claim 4, further comprising using one or more tumor specific mutations as defined in claim 4, in any one or both of the marker genes cKIT (GenBank acc. no. NM_000222.2) and PDGFRA (GenBank acc. no. NM_006206.4) as a panel of molecular markers for obtaining quantitative information for diagnosing and/or monitoring a gastrointestinal stromal tumor.

11. The method of claim 5, further comprising using one or more tumor specific mutations as defined in claim 5, in any one or both of the marker genes cKIT (GenBank acc. no. NM_000222.2) and PDGFRA (GenBank acc. no. NM_006206.4) as a panel of molecular markers for obtaining quantitative information for diagnosing and/or monitoring a gastrointestinal stromal tumor.

12. The method of claim 7, further comprising using one or more tumor specific mutations as defined in claim 7, in any one or both of the marker genes cKIT (GenBank acc. no. NM_000222.2) and PDGFRA (GenBank acc. no.

NM_006206.4) as a panel of molecular markers for obtaining quantitative information for diagnosing and/or monitoring a gastrointestinal stromal tumor.

13. The method of claim 7, wherein the PCR technique is ligation-PCR.

* * * * *

SEQUENCE LISTING

<160> NUMBER OF SEQ ID NOS: 24

<210> SEQ ID NO 1
<211> LENGTH: 2931
<212> TYPE: DNA
<213> ORGANISM: Homo sapiens
<220> FEATURE:
<221> NAME/KEY: misc_feature
<223> OTHER INFORMATION: CDS of the cKIT marker gene

<400> SEQUENCE: 1

| | | | | | |
|---|---|---|---|---|---|
| atgagaggcg | ctcgcggcgc | ctgggatttt | ctctgcgttc | tgctcctact | gcttcgcgtc | 60 |
| cagacaggct | cttctcaacc | atctgtgagt | ccaggggaac | cgtctccacc | atccatccat | 120 |
| ccaggaaaat | cagacttaat | agtccgcgtg | ggcgacgaga | ttaggctgtt | atgcactgat | 180 |
| ccgggctttg | tcaaatggac | ttttgagatc | ctggatgaaa | cgaatgagaa | taagcagaat | 240 |
| gaatggatca | cggaaaaggc | agaagccacc | aacaccggca | atacacgtg | caccaacaaa | 300 |
| cacggcttaa | gcaattccat | ttatgtgttt | gttagagatc | ctgccaagct | tttccttgtt | 360 |
| gaccgctcct | tgtatgggaa | agaagacaac | gacacgctgg | tccgctgtcc | tctcacagac | 420 |
| ccagaagtga | ccaattattc | cctcaagggg | tgccagggga | agcctcttcc | caaggacttg | 480 |
| aggtttattc | ctgaccccaa | ggcgggcatc | atgatcaaaa | gtgtgaaacg | cgcctaccat | 540 |
| cggctctgtc | tgcattgttc | tgtggaccag | gagggcaagt | cagtgctgtc | ggaaaaattc | 600 |
| atcctgaaag | tgaggccagc | cttcaaagct | gtgcctgttg | tgtctgtgtc | caaagcaagc | 660 |
| tatcttctta | gggaagggga | agaattcaca | gtgacgtgca | caataaaaga | tgtgtctagt | 720 |
| tctgtgtact | caacgtggaa | aagagaaaac | agtcagacta | aactacagga | gaaatataat | 780 |
| agctggcatc | acggtgactt | caattatgaa | cgtcaggcaa | cgttgactat | cagttcagcg | 840 |
| agagttaatg | attctggagt | gttcatgtgt | tatgccaata | atacttttgg | atcagcaaat | 900 |
| gtcacaacaa | ccttggaagt | agtagataaa | ggattcatta | atatcttccc | catgataaac | 960 |
| actacagtat | ttgtaaacga | tggagaaaat | gtagatttga | ttgttgaata | tgaagcattc | 1020 |
| cccaaacctg | aacaccagca | gtggatctat | atgaacagaa | ccttcactga | taatggggaa | 1080 |
| gattatccca | gtctgagaa | tgaaagtaat | atcagatacg | taagtgaact | tcatctaacg | 1140 |
| agattaaaag | gcaccgaagg | aggcacttac | acattcctag | tgtccaattc | tgacgtcaat | 1200 |
| gctgccatag | catttaatgt | ttatgtgaat | acaaaaccag | aaatcctgac | ttacgacagg | 1260 |
| ctcgtgaatg | gcatgctcca | atgtgtggca | gcaggattcc | cagagcccac | aatagattgg | 1320 |
| tattttgtc | aggaactga | gcagagatgc | tctgcttctg | tactgccagt | ggatgtgcag | 1380 |
| acactaaact | catctgggcc | accgtttgga | aagctagtgg | ttcagagttc | tatagattct | 1440 |
| agtgcattca | agcacaatgg | cacggttgaa | tgtaaggctt | acaacgatgt | gggcaagact | 1500 |
| tctgcctatt | ttaactttgc | atttaaaggt | aacaacaaag | agcaaatcca | tcccacacc | 1560 |
| ctgttcactc | ctttgctgat | ggtttcgta | atcgtagctg | gcatgatgtg | cattattgtg | 1620 |
| atgattctga | cctacaaata | tttacagaaa | cccatgtatg | aagtacagtg | gaaggttgtt | 1680 |
| gaggagataa | atggaaacaa | ttatgtttac | atagacccaa | cacaacttcc | ttatgatcac | 1740 |
| aaatgggagt | tcccagaaa | caggctgagt | tttgggaaaa | ccctgggtgc | tggagctttc | 1800 |
| gggaaggttg | ttgaggcaac | tgcttatggc | ttaattaagt | cagatgcggc | catgactgtc | 1860 |
| gctgtaaaga | tgctcaagcc | gagtgcccat | ttgacagaac | gggaagccct | catgtctgaa | 1920 |
| ctcaaagtcc | tgagttacct | tggtaatcac | atgaatattg | tgaatctact | ggagcctgc | 1980 |

| | |
|---|---|
| accattggag ggcccaccct ggtcattaca gaatattgtt gctatggtga tcttttgaat | 2040 |
| tttttgagaa gaaaacgtga ttcatttatt tgttcaaagc aggaagatca tgcagaagct | 2100 |
| gcactttata agaatcttct gcattcaaag gagtcttcct gcagcgatag tactaatgag | 2160 |
| tacatggaca tgaaacctgg agtttcttat gttgtcccaa ccaaggccga caaaaggaga | 2220 |
| tctgtgagaa taggctcata catagaaaga gatgtgactc ccgccatcat ggaggatgac | 2280 |
| gagttggccc tagacttaga agacttgctg agcttttctt accaggtggc aaagggcatg | 2340 |
| gctttcctcg cctccaagaa ttgtattcac agagacttgg cagccagaaa tatcctcctt | 2400 |
| actcatggtc ggatcacaaa gatttgtgat tttggtctag ccagagacat caagaatgat | 2460 |
| tctaattatg tggttaaagg aaacgctcga ctacctgtga agtggatggc acctgaaagc | 2520 |
| attttcaact gtgtatacac gtttgaaagt gacgtctggt cctatgggat tttctcttgg | 2580 |
| gagctgttct cttaggaag cagcccctat cctggaatgc cggtcgattc taagttctac | 2640 |
| aagatgatca aggaaggctt ccggatgctc agccctgaac acgcacctgc tgaaatgtat | 2700 |
| gacataatga agacttgctg ggatgcagat ccctaaaaa gaccaacatt caagcaaatt | 2760 |
| gttcagctaa ttgagaagca gatttcagag agcaccaatc atatttactc caacttagca | 2820 |
| aactgcagcc ccaaccgaca gaagcccgtg gtagaccatt ctgtgcggat caattctgtc | 2880 |
| ggcagcaccg cttcctcctc ccagcctctg cttgtgcacg acgatgtctg a | 2931 |

<210> SEQ ID NO 2
<211> LENGTH: 6574
<212> TYPE: DNA
<213> ORGANISM: Homo sapiens
<220> FEATURE:
<221> NAME/KEY: misc_feature
<223> OTHER INFORMATION: CDS of the PDGFRA marker gene

<400> SEQUENCE: 2

| | |
|---|---|
| aagagcaaaa agcgaaggcg caatctggac actgggagat tcggagcgca gggagtttga | 60 |
| gagaaacttt tattttgaag agaccaaggt tgaggggggg cttatttcct gacagctatt | 120 |
| tacttagagc aaatgattag ttttagaagg atggactata acattgaatc aattacaaaa | 180 |
| cgcggttttt gagcccatta ctgttggagc tacaggagag aaacagagg aggagactgc | 240 |
| aagagatcat tggaggccgt gggcacgctc tttactccat gtgtgggaca ttcattgcgg | 300 |
| aataacatcg gaggagaagt ttcccagagc tatgggggact tcccatccgg cgttcctggt | 360 |
| cttaggctgt cttctcacag ggctgagcct aatcctctgc cagctttcat tacctctat | 420 |
| ccttccaaat gaaaatgaaa aggttgtgca gctgaattca tccttttctc tgagatgctt | 480 |
| tggggagagt gaagtgagct ggcagtaccc catgtctgaa gaagagagct ccgatgtgga | 540 |
| aatcagaaat gaagaaaaca acagcggcct ttttgtgacg gtcttggaag tgagcagtgc | 600 |
| ctcggcggcc cacacagggt tgtacacttg ctattacaac cacactcaga cagaagagaa | 660 |
| tgagcttgaa gcaggcaca tttacatcta tgtgccagac ccagatgtag cctttgtacc | 720 |
| tctaggaatg acggattatt tagtcatcgt ggaggatgat gattctgcca ttataccttg | 780 |
| tcgcacaact gatcccgaga ctcctgtaac cttacacaac agtgagggg tggtacctgc | 840 |
| ctcctacgac agcagacagg gctttaatgg gaccttcact gtagggcct atatctgtga | 900 |
| ggccaccgtc aaaggaaaga agttccagac catcccattt aatgtttatg ctttaaaagc | 960 |
| aacatcagag ctggatctag aaatggaagc tcttaaaacc gtgtataagt caggggaaac | 1020 |
| gattgtggtc acctgtgctg tttttaacaa tgaggtggtt gaccttcaat ggactttaccc | 1080 |

-continued

```
tggagaagtg aaaggcaaag gcatcacaat gctggaagaa atcaaagtcc catccatcaa   1140
attggtgtac actttgacgg tccccgaggc cacggtgaaa gacagtggag attacgaatg   1200
tgctgcccgc caggctacca gggaggtcaa agaaatgaag aaagtcacta tttctgtcca   1260
tgagaaaggt ttcattgaaa tcaaacccac cttcagccag ttggaagctg tcaacctgca   1320
tgaagtcaaa cattttgttg tagaggtgcg ggcctaccca cctcccagga tatcctggct   1380
gaaaaacaat ctgactctga ttgaaaatct cactgagatc accactgatg tggaaaagat   1440
tcaggaaata aggtatcgaa gcaaattaaa gctgatccgt gctaaggaag aagacagtgg   1500
ccattatact attgtagctc aaaatgaaga tgctgtgaag agctatactt ttgaactgtt   1560
aactcaagtt ccttcatcca ttctggactt ggtcgatgat caccatggct caactggggg   1620
acagacggtg aggtgcacag ctgaaggcac gccgcttcct gatattgagt ggatgatatg   1680
caaagatatt aagaaatgta ataatgaaac ttcctggact attttggcca acaatgtctc   1740
aaacatcatc acggagatcc actcccgaga caggagtacc gtggagggcc gtgtgacttt   1800
cgccaaagtg gaggagacca tcgccgtgcg atgcctggct aagaatctcc ttggagctga   1860
gaaccgagag ctgaagctgg tggctcccac cctgcgttct gaactcacgg tggctgctgc   1920
agtcctggtg ctgttggtga ttgtgatcat ctcacttatt gtcctggttg tcatttggaa   1980
acagaaaccg aggtatgaaa ttcgctggag ggtcattgaa tcaatcagcc cagatggaca   2040
tgaatatatt tatgtggacc cgatgcagct gccttatgac tcaagatggg agtttccaag   2100
agatggacta gtgcttggtc gggtcttggg gtctggagcg tttgggaagg tggttgaagg   2160
aacagcctat ggattaagcc ggtcccaacc tgtcatgaaa gttgcagtga agatgctaaa   2220
acccacggcc agatccagtg aaaaacaagc tctcatgtct gaactgaaga taatgactca   2280
cctgggccca catttgaaca ttgtaaactt gctgggagcc tgcaccaagt caggcccccat   2340 ttacatcatc acagagtatt gcttctatgg agatttggtc aactatttgc ataagaatag   2400
ggatagcttc ctgagccacc acccagagaa gccaaagaaa gagctggata tctttggatt   2460
gaaccctgct gatgaaagca cacggagcta tgttatttta tcttttgaaa acaatggtga   2520
ctacatggac atgaagcagg ctgatactac acagtatgtc cccatgctag aaaggaagaa   2580
ggtttctaaa tattccgaca tccagagatc actctatgat cgtccagcct catataagaa   2640
gaaatctatg ttagactcag aagtcaaaaa cctcctttca gatgataact cagaaggcct   2700
tactttattg gatttgttga gcttcaccta tcaagttgcc cgaggaatgg agttttttggc   2760 ttcaaaaaat tgtgtccacc gtgatctggc tgctcgcaac gtcctcctgg cacaaggaaa   2820
aattgtgaag atctgtgact ttggcctggc cagagacatc atgcatgatt cgaactatgt   2880
gtcgaaaggc agtacctttc tgcccgtgaa gtggatggct cctgagagca tctttgacaa   2940
cctctacacc acactgagtg atgtctggtc ttatggcatt ctgctctggg agatcttttc   3000
ccttggtggc ccccttacc ccggcatgat ggtggattct actttctaca ataagatcaa   3060
gagtgggtac cggatggcca agcctgacca cgctaccagt gaagtctacg agatcatggt   3120
gaaatgctgg aacagtgagc cggagaagag accctccttt taccacctga gtgagattgt   3180
ggagaatctg ctgcctggac aatataaaaa gagttatgaa aaaattcacc tggacttcct   3240
gaagagtgac catcctgctg tggcacgcat gcgtgtggac tcagacaatg catacattgg   3300
tgtcacctac aaaaacgagg aagacaagct gaaggactgg gagggtggtc tggatgagca   3360
gagactgagc gctgacagtg gctacatcat tcctctgcct gacattgacc ctgtccctga   3420
ggaggaggac ctgggcaaga ggaacagaca cagctcgcag acctctgaag agagtgccat   3480
```

```
tgagacgggt tccagcagtt ccaccttcat caagagagag gacgagacca ttgaagacat    3540
cgacatgatg gatgacatcg gcatagactc ttcagacctg gtggaagaca gcttcctgta    3600
actggcggat tcgaggggtt ccttccactt ctggggccac ctctggatcc cgttcagaaa    3660
accactttat tgcaatgcag aggttgagag gaggacttgg ttgatgttta agagaagtt    3720 cccagccaag ggcctcgggg agcgttctaa atatgaatga atgggatatt ttgaaatgaa    3780
ctttgtcagt gttgcctctt gcaatgcctc agtagcatct cagtggtgtg tgaagtttgg    3840
agatagatgg ataagggaat aataggccac agaaggtgaa ctttgtgctt caaggacatt    3900
ggtgagagtc caacgacac aatttatact gcgacagaac ttcagcattg taattatgta    3960
aataactcta accaaggctg tgtttagatt gtattaacta tcttctttgg acttctgaag    4020
agaccactca atccatccat gtacttccct cttgaaacct gatgtcagct gctgttgaac    4080 ttttttaaaga agtgcatgaa aaaccatttt tgaaccttaa aaggtactgg tactatagca    4140
ttttgctatc ttttttagtg ttaaagagat aagaataat aattaaccaa ccttgtttaa    4200
tagatttggg tcatttagaa gcctgacaac tcattttcat attgtaatct atgtttataa    4260
tactactact gttatcagta atgctaaatg tgtaataatg taacatgatt tccctccaga    4320
gaaagcacaa tttaaaacaa tccttactaa gtaggtgatg agtttgacag ttttttgacat    4380 ttatattaaa taacatgttt ctctataaag tatggtaata gctttagtga attaaattta    4440
gttgagcata gagaacaaag taaaagtagt gttgtccagg aagtcagaat ttttaactgt    4500
actgaatagg ttccccaatc catcgtatta aaaaacaatt aactgccctc tgaaataatg    4560
ggattagaaa caaacaaaac tcttaagtcc taaaagttct caatgtagag gcataaacct    4620
gtgctgaaca taacttctca tgtatattac ccaatggaaa atataatgat cagcaaaaag    4680
actggatttg cagaagtttt ttttttttt ttcttcatgc ctgatgaaag ctttggcgac    4740
cccaatatat gtatttttg aatctatgaa cctgaaaagg gtcagaagga tgcccagaca    4800
tcagcctcct tctttcaccc cttaccccaa agagaaagag tttgaaactc gagaccataa    4860
agatattctt tagtggaggc tggatgtgca ttagcctgga tcctcagttc tcaaatgtgt    4920
gtggcagcca ggatgactag atcctgggtt tccatccttg agattctgaa gtatgaagtc    4980
tgagggaaac cagagtctgt attttctaa actccctggc tgttctgatc ggccagtttt    5040
cggaaacact gacttaggtt tcaggaagtt gccatggaa acaaataatt tgaactttgg    5100
aacagggttg gcattcaacc acgcaggaag cctactattt aaatccttgg cttcaggtta    5160
gtgacattta atgccatcta gctagcaatt gcgacccttaa tttaactttc cagtcttagc    5220
tgaggctgag aaagctaaag tttggttttg acaggttttc caaaagtaaa gatgctactt    5280
cccactgtat gggggagatt gaactttccc cgtctcccgt cttctgcctc ccactccata    5340
ccccgccaag gaaaggcatg tacaaaaatt atgcaattca gtgttccaag tctctgtgta    5400
accagctcag tgttttggtg gaaaaaacat tttaagtttt actgataatt tgaggttaga    5460
tgggaggatg aattgtcaca tctatccaca ctgtcaaaca ggttggtgtg ggttcattgg    5520
cattctttgc aatactgctt aattgctgat accatatgaa tgaaacatgg gctgtgatta    5580
ctgcaatcac tgtgctatcg gcagatgatg ctttggaaga tgcagaagca ataataaagt    5640
acttgactac ctactggtgt aatctcaatg caagccccaa cttcttatc caacttttc    5700 atagtaagtg cgaagactga gccagattgg ccaattaaaa acgaaaacct gactaggttc    5760
tgtagagcca attagacttg aaatacgttt gtgtttctag aatcacagct caagcattct    5820
```

```
gtttatcgct cactctccct tgtacagcct tattttgttg gtgctttgca tttttgatatt    5880 gctgtgagcc ttgcatgaca tcatgaggcc ggatgaaact tctcagtcca gcagtttcca    5940
gtcctaacaa atgctcccac ctgaatttgt atatgactgc atttgtgtgt gtgtgtgtgt    6000
tttcagcaaa ttccagattt gtttcctttt ggcctcctgc aaagtctcca gaagaaaatt    6060
tgccaatctt tcctactttc tatttttatg atgacaatca aagccggcct gagaaacact    6120
atttgtgact ttttaaacga ttagtgatgt ccttaaaatg tggtctgcca atctgtacaa    6180
aatggtccta ttttttgtgaa gagggacata agataaaatg atgttataca tcaatatgta    6240
tatatgtatt tctatataga cttggagaat actgccaaaa catttatgac aagctgtatc    6300
actgccttcg tttatatttt tttaactgtg ataatcccca caggcacatt aactgttgca    6360
cttttgaatg tccaaaattt atatttaga aataataaaa agaaagatac ttacatgttc    6420
ccaaaacaat ggtgtggtga atgtgtgaga aaaactaact tgatagggtc taccaataca    6480
aaatgtatta cgaatgcccc tgttcatgtt tttgttttaa aacgtgtaaa tgaagatctt    6540
tatatttcaa taaatgatat ataatttaaa gtta                                6574

<210> SEQ ID NO 3
<211> LENGTH: 45
<212> TYPE: DNA
<213> ORGANISM: Artificial Sequence
<220> FEATURE:
<223> OTHER INFORMATION: Artificially synthesized oligonucleotide primer
<220> FEATURE:
<221> NAME/KEY: misc_feature
<223> OTHER INFORMATION: oligonucleotide primer cKitV559D_1

<400> SEQUENCE: 3
gggttcccta agggttggac ccatgtatga agtacagtgg aagga                    45

<210> SEQ ID NO 4
<211> LENGTH: 63
<212> TYPE: DNA
<213> ORGANISM: Artificial Sequence
<220> FEATURE:
<223> OTHER INFORMATION: Artificially synthesized oligonucleotide primer
<220> FEATURE:
<221> NAME/KEY: misc_feature
<223> OTHER INFORMATION: oligonucleotide primer cKitV559D_2

<400> SEQUENCE: 4
tgttgaggag ataaatggaa acaattatgt ttacatggcg tctagattgg atcttgctgg    60
cac                                                                  63

<210> SEQ ID NO 5
<211> LENGTH: 46
<212> TYPE: DNA
<213> ORGANISM: Artificial Sequence
<220> FEATURE:
<223> OTHER INFORMATION: Artificially synthesized oligonucleotide primer
<220> FEATURE:
<221> NAME/KEY: misc_feature
<223> OTHER INFORMATION: oligonucleotide primer cKit-wt_1

<400> SEQUENCE: 5
gggttcccta agggttggac gtagctggca tgatgtgcat tattgt                   46

<210> SEQ ID NO 6
<211> LENGTH: 59
<212> TYPE: DNA
<213> ORGANISM: Artificial Sequence
<220> FEATURE:
```

-continued

```
<223> OTHER INFORMATION: Artificially synthesized oligonucleotide primer
<220> FEATURE:
<221> NAME/KEY: misc_feature
<223> OTHER INFORMATION: oligonucleotide primer cKit-wt_2

<400> SEQUENCE: 6
gatgattctg acctacaaat atttacaggt aaccattcta gattggatct tgctggcac      59

<210> SEQ ID NO 7
<211> LENGTH: 22
<212> TYPE: DNA
<213> ORGANISM: Artificial Sequence
<220> FEATURE:
<223> OTHER INFORMATION: Artificially synthesized oligonucleotide primer
<220> FEATURE:
<221> NAME/KEY: misc_feature
<223> OTHER INFORMATION: oligonucleotide primer cKit_f

<400> SEQUENCE: 7
caccctgttc actcctttgc tg                                              22

<210> SEQ ID NO 8
<211> LENGTH: 27
<212> TYPE: DNA
<213> ORGANISM: Artificial Sequence
<220> FEATURE:
<223> OTHER INFORMATION: Artificially synthesized oligonucleotide primer
<220> FEATURE:
<221> NAME/KEY: misc_feature
<223> OTHER INFORMATION: oligonucleotide primer cKit_r1

<400> SEQUENCE: 8
cccatttgtg atcataagga agttgtg                                         27

<210> SEQ ID NO 9
<211> LENGTH: 26
<212> TYPE: DNA
<213> ORGANISM: Artificial Sequence
<220> FEATURE:
<223> OTHER INFORMATION: Artificially synthesized oligonucleotide primer
<220> FEATURE:
<221> NAME/KEY: misc_feature
<223> OTHER INFORMATION: oligonucleotide primer cKit_r2

<400> SEQUENCE: 9
aaaactcagc ctgtttctgg gaaact                                          26

<210> SEQ ID NO 10
<211> LENGTH: 60
<212> TYPE: DNA
<213> ORGANISM: Artificial Sequence
<220> FEATURE:
<223> OTHER INFORMATION: Artificially synthesized oligonucleotide

<400> SEQUENCE: 10
accaacacaa cttccttatg atcacaaatg ggagtttccc agaaacaggc tgagttttgg      60

<210> SEQ ID NO 11
<211> LENGTH: 42
<212> TYPE: DNA
<213> ORGANISM: Artificial Sequence
<220> FEATURE:
<223> OTHER INFORMATION: Artificially synthesized oligonucleotide

<400> SEQUENCE: 11
gcaaacaaca caacttcctt atgatcacaa atgggagttt cc                        42
```

```
<210> SEQ ID NO 12
<211> LENGTH: 42
<212> TYPE: DNA
<213> ORGANISM: Artificial Sequence
<220> FEATURE:
<223> OTHER INFORMATION: Artificially synthesized oligonucleotide

<400> SEQUENCE: 12
tcccaacaca acttccttat gatcacaaat gggagtttcc ca                           42

<210> SEQ ID NO 13
<211> LENGTH: 45
<212> TYPE: DNA
<213> ORGANISM: Artificial Sequence
<220> FEATURE:
<223> OTHER INFORMATION: Artificially synthesized oligonucleotide

<400> SEQUENCE: 13
acaacttcct tatgatcaca aatgggagtt tcccagaaac aggct                        45

<210> SEQ ID NO 14
<211> LENGTH: 27
<212> TYPE: DNA
<213> ORGANISM: Artificial Sequence
<220> FEATURE:
<223> OTHER INFORMATION: Artificially synthesized oligonucleotide

<400> SEQUENCE: 14
aaacccatgt atgaagtaca gtggaag                                            27

<210> SEQ ID NO 15
<211> LENGTH: 53
<212> TYPE: DNA
<213> ORGANISM: Artificial Sequence
<220> FEATURE:
<223> OTHER INFORMATION: Artificially synthesized oligonucleotide
      deletion/insertion
<220> FEATURE:
<221> NAME/KEY: misc_feature
<222> LOCATION: (1)..(53)
<223> OTHER INFORMATION: nucleotides 1-52 are deleted and replaced with
      nucleotide 53 at codons K550-K558 of the cKIT marker gene

<400> SEQUENCE: 15
acagtggaag gttgttgagg agataaatgg aaacaattat gtttacatag acg              53

<210> SEQ ID NO 16
<211> LENGTH: 12
<212> TYPE: DNA
<213> ORGANISM: Artificial Sequence
<220> FEATURE:
<223> OTHER INFORMATION: Artificially synthesized oligonucleotide

<400> SEQUENCE: 16
cccatgtatg aa                                                            12

<210> SEQ ID NO 17
<211> LENGTH: 18
<212> TYPE: DNA
<213> ORGANISM: Artificial Sequence
<220> FEATURE:
<223> OTHER INFORMATION: Artificially synthesized oligonucleotide
```

```
<400> SEQUENCE: 17
tatgaagtac agtggaag                                                 18

<210> SEQ ID NO 18
<211> LENGTH: 54
<212> TYPE: DNA
<213> ORGANISM: Artificial Sequence
<220> FEATURE:
<223> OTHER INFORMATION: Artificially synthesized oligonucleotide

<400> SEQUENCE: 18
gaagtacagt ggaaggttgt tgaggagata aatggaaaca attatgttta cata         54

<210> SEQ ID NO 19
<211> LENGTH: 57
<212> TYPE: DNA
<213> ORGANISM: Artificial Sequence
<220> FEATURE:
<223> OTHER INFORMATION: Artificially synthesized oligonucleotide

<400> SEQUENCE: 19
acccaacaca acttccttat gatcacaaat gggagtttcc cagaaacagg ctgagtt      57

<210> SEQ ID NO 20
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 20
gtatgaagta cagtggaagg t                                             21

<210> SEQ ID NO 21
<211> LENGTH: 57
<212> TYPE: DNA
<213> ORGANISM: Artificial Sequence
<220> FEATURE:
<223> OTHER INFORMATION: Artificially synthesized oligonucleotide

<400> SEQUENCE: 21
tgaagtacag tggaaggttg ttgaggagat aaatggaaac aattatgttt acataga      57

<210> SEQ ID NO 22
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 22
tgaagtacag tggaaggttg ttga                                          24

<210> SEQ ID NO 23
<211> LENGTH: 57
<212> TYPE: DNA
<213> ORGANISM: Artificial Sequence
<220> FEATURE:
<223> OTHER INFORMATION: Artificially synthesized oligonucleotide

<400> SEQUENCE: 23
gttgaggaga taaatggaaa caattatgtt tacatagacc caacacaact tccttat      57

<210> SEQ ID NO 24
<211> LENGTH: 21
```

```
<212> TYPE: DNA
<213> ORGANISM: Artificial Sequence
<220> FEATURE:
<223> OTHER INFORMATION: Artificially synthesized oligonucleotide

<400> SEQUENCE: 24
acacaacttc cttatgatca c                                             21
```